United States Patent
Xie et al.

(10) Patent No.: US 8,681,331 B2
(45) Date of Patent: Mar. 25, 2014

(54) SYSTEMS AND METHODS PROVIDING EFFICIENT DETECTION OF BACK-SCATTERED ILLUMINATION IN MODULATION TRANSFER MICROSCOPY OR MICRO-SPECTROSCOPY

(71) Applicant: President and Fellows of Harvard College, Cambridge, MA (US)

(72) Inventors: Sunney Xiaoliang Xie, Lexington, MA (US); Christian W. Freudiger, Boston, MA (US); Brian G. Saar, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/719,717

(22) Filed: Dec. 19, 2012

(65) Prior Publication Data

US 2013/0162994 A1   Jun. 27, 2013

Related U.S. Application Data

(63) Continuation of application No. PCT/US2010/054925, filed on Nov. 1, 2010.

(60) Provisional application No. 61/357,356, filed on Jun. 22, 2010, provisional application No. 61/362,003, filed on Jul. 7, 2010.

(51) Int. Cl.
*G01N 21/00* (2006.01)
*G01N 21/53* (2006.01)

(52) U.S. Cl.
CPC ........................... *G01N 21/53* (2013.01)
USPC .......................................... 356/337; 356/342

(58) Field of Classification Search
CPC ............................... G01N 21/00; G01N 21/53
USPC .................................................. 356/432–442
See application file for complete search history.

(56) References Cited

U.S. PATENT DOCUMENTS

| 5,124,835 A | 6/1992 | Shibaguchi et al. |
| 6,798,507 B2 | 9/2004 | Xie et al. |
| 6,809,814 B2 | 10/2004 | Xie et al. |
| 7,352,458 B2 | 4/2008 | Xie et al. |

(Continued)

OTHER PUBLICATIONS

Freudiger et al., "Label-Free Biomedical Imaging with High-Sensitivity by Stimulated Raman Scattering Microscopy" Science 1, Dec. 19, 2008, vol. 322, No. 5909, pp. 1857-1861.

(Continued)

*Primary Examiner* — Michael P Stafira
(74) *Attorney, Agent, or Firm* — Gesmer Updegrove LLP

(57) ABSTRACT

A microscopy or micro-spectroscopy system is disclosed that includes a first light source, a second light source, a modulator, an optical assembly and a processor. The first light source is for providing a first illumination field at a first optical frequency $\omega_1$ and the second light source is for providing a second illumination field at a second optical frequency $\omega_2$. The modulator is for modulating a property of the second illumination field at a modulation frequency f of at least 100 kHz to provide a modulated second illumination field. The optical assembly includes focusing optics and an optical detector system. The focusing optics is for directing and focusing the first illumination field and the modulated second illumination field through an objective lens toward the common focal volume along an excitation path.

42 Claims, 19 Drawing Sheets

(56) References Cited

U.S. PATENT DOCUMENTS

| | | | |
|---|---|---|---|
| 2003/0067607 A1* | 4/2003 | Wolleschensky et al. | 356/484 |
| 2004/0156053 A1* | 8/2004 | Wolleschensky et al. | 356/485 |
| 2008/0037595 A1 | 2/2008 | Gankkhanov et al. | |
| 2009/0073432 A1 | 3/2009 | Bahram et al. | |
| 2010/0046039 A1* | 2/2010 | Xie et al. | 358/471 |
| 2010/0188496 A1 | 7/2010 | Xie et al. | |
| 2010/0252750 A1 | 10/2010 | Xie et al. | |

OTHER PUBLICATIONS

Andreas Volkmer, "Vibrational imaging and microspectroscopies based on coherent anti-Stokes Raman scattering microscopy" Journal of Physics D: Applied Physics, 2005, vol. 38, No. 5, pp. R64, R65, R68, R69.

Krishnamachari et al., "Detecting lateral interfaces with focus-engineered coherent anti-Stokes Raman scattering microscopy" Journal of Raman Spectroscopy, 2008, pp. 593-598.

Piyawattanametha et al., "Fast-scanning two-photon fluorescence imaging based on a microelectromechanical systems two-dimensional scanning mirror" Optics Letters 21(13)2018, Jul. 1, 2006, pp. 1-7.

Lee et al., "Scanning fiber endoscopy with highly flexible, 1mm catheterscopes for wide-field, full color imaging" Journal of BioPhotonics 3., No. 5-6, 2010, pp. 385-407.

International Search Report and Written Opinion issued in connection with PCT Application No. PCT/US2010/054925, mailed on Jul. 26, 2011.

* cited by examiner

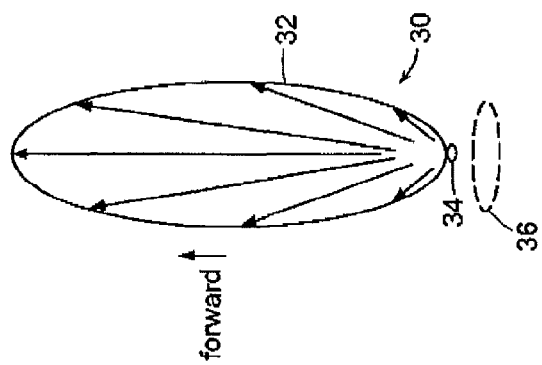
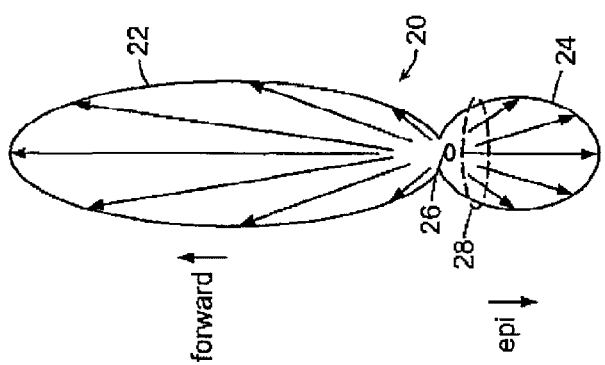
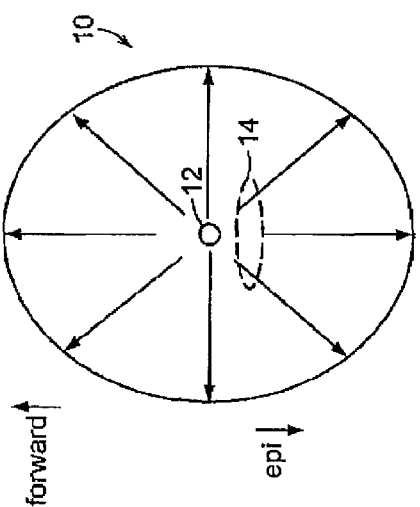
FIG. 1C PRIOR ART
FIG. 1B PRIOR ART
FIG. 1A PRIOR ART

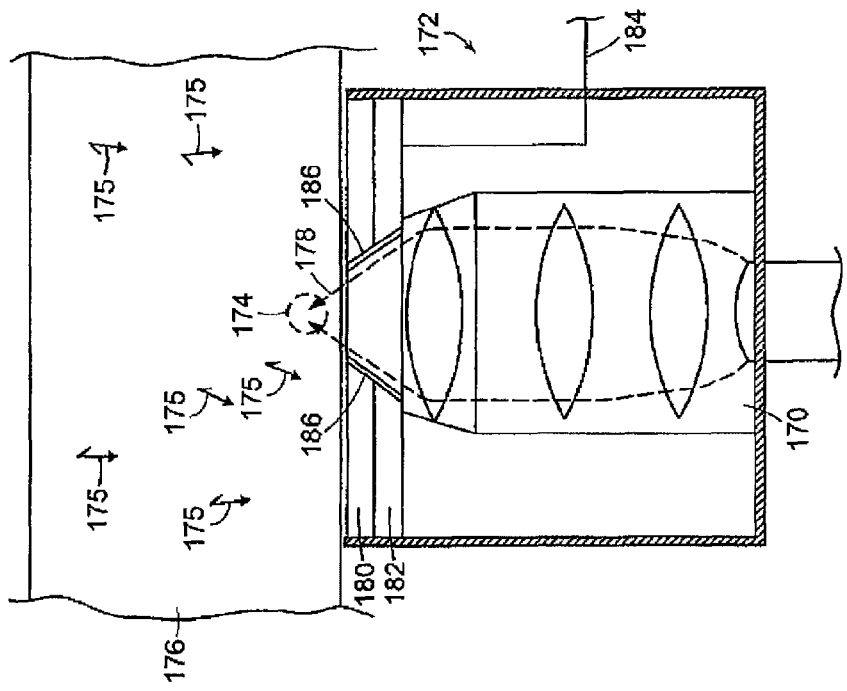
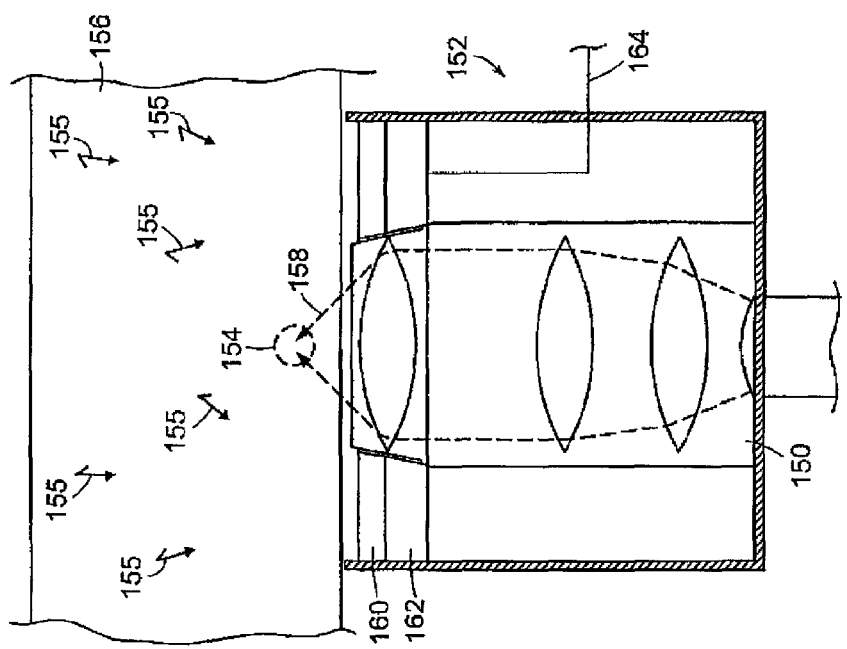

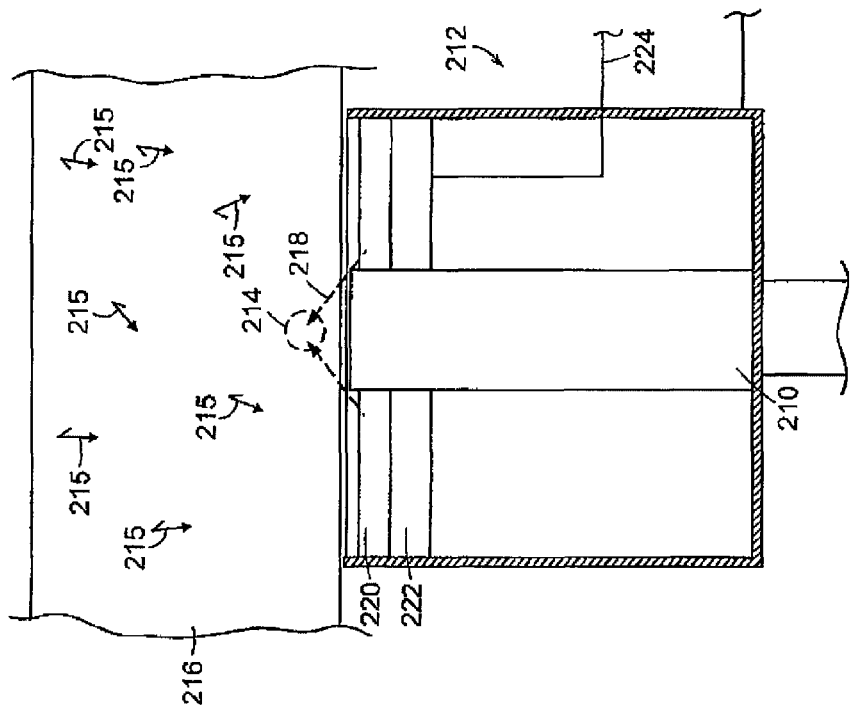
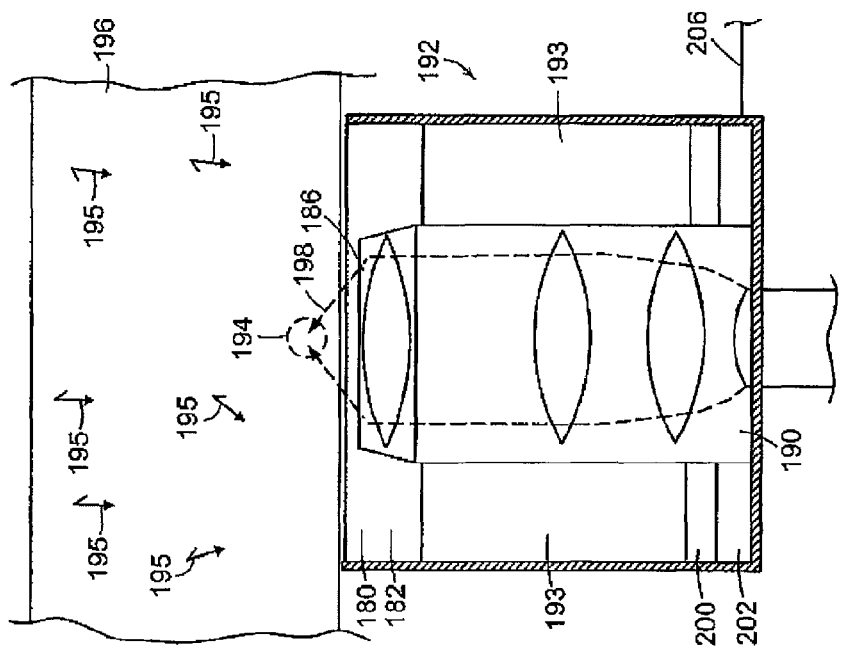

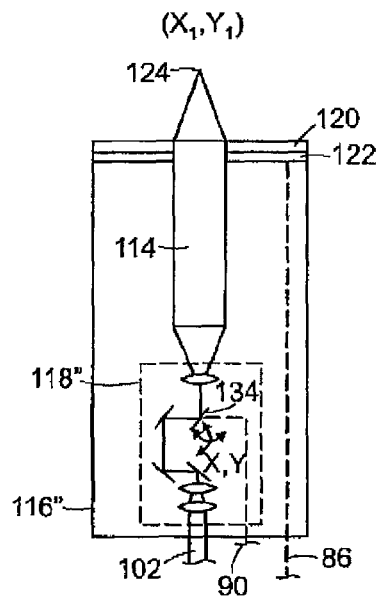 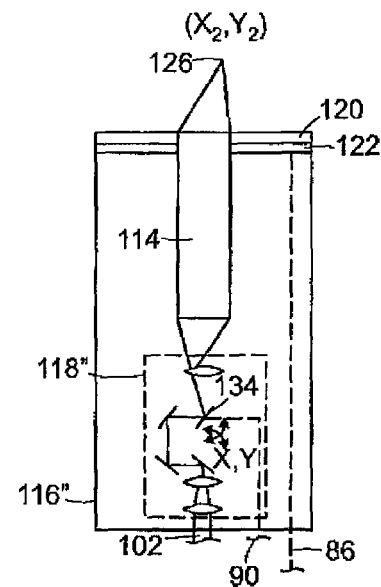
FIG. 10A  FIG. 10B
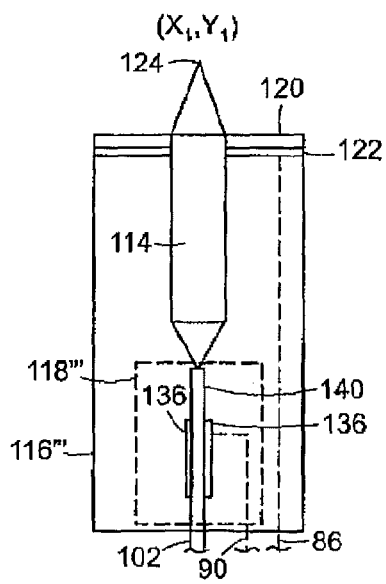 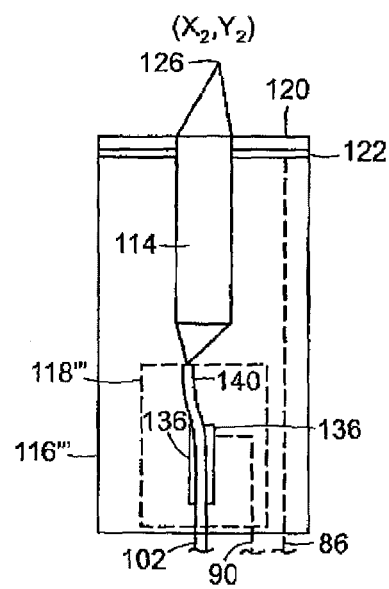
FIG. 11A  FIG. 11B

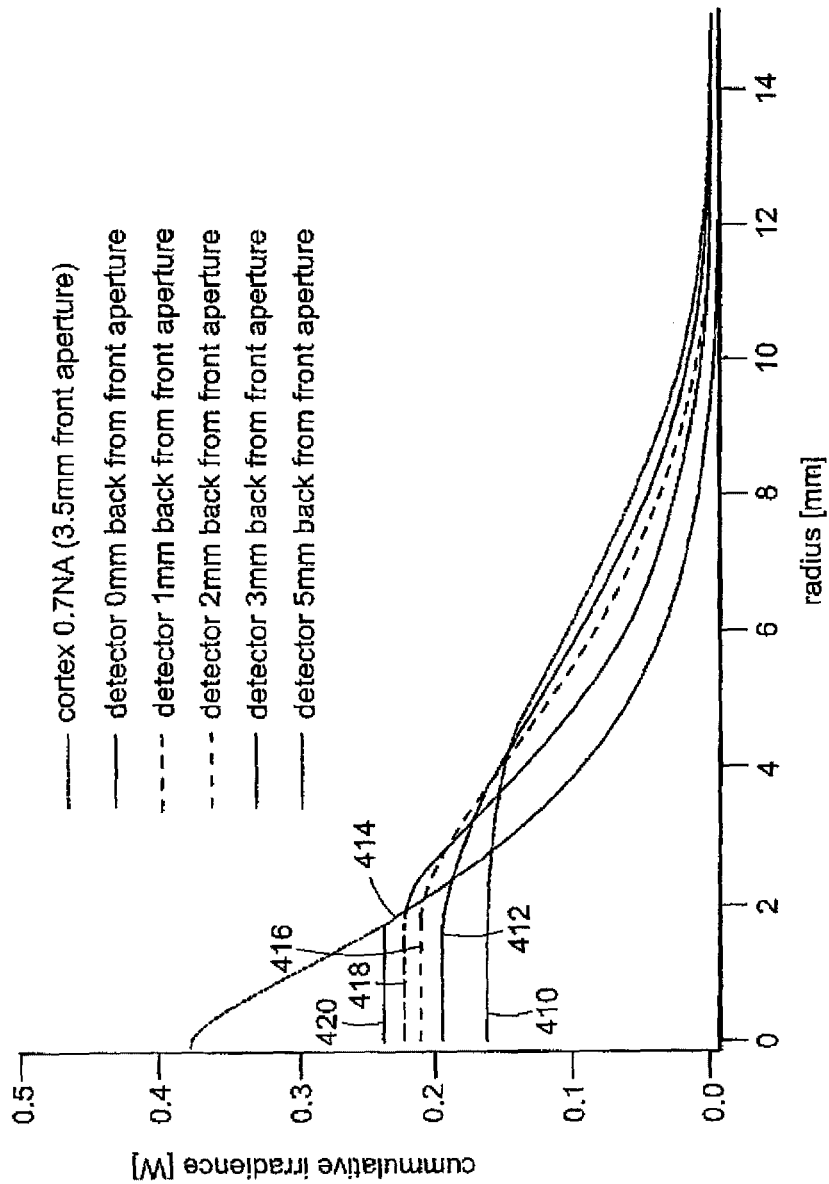

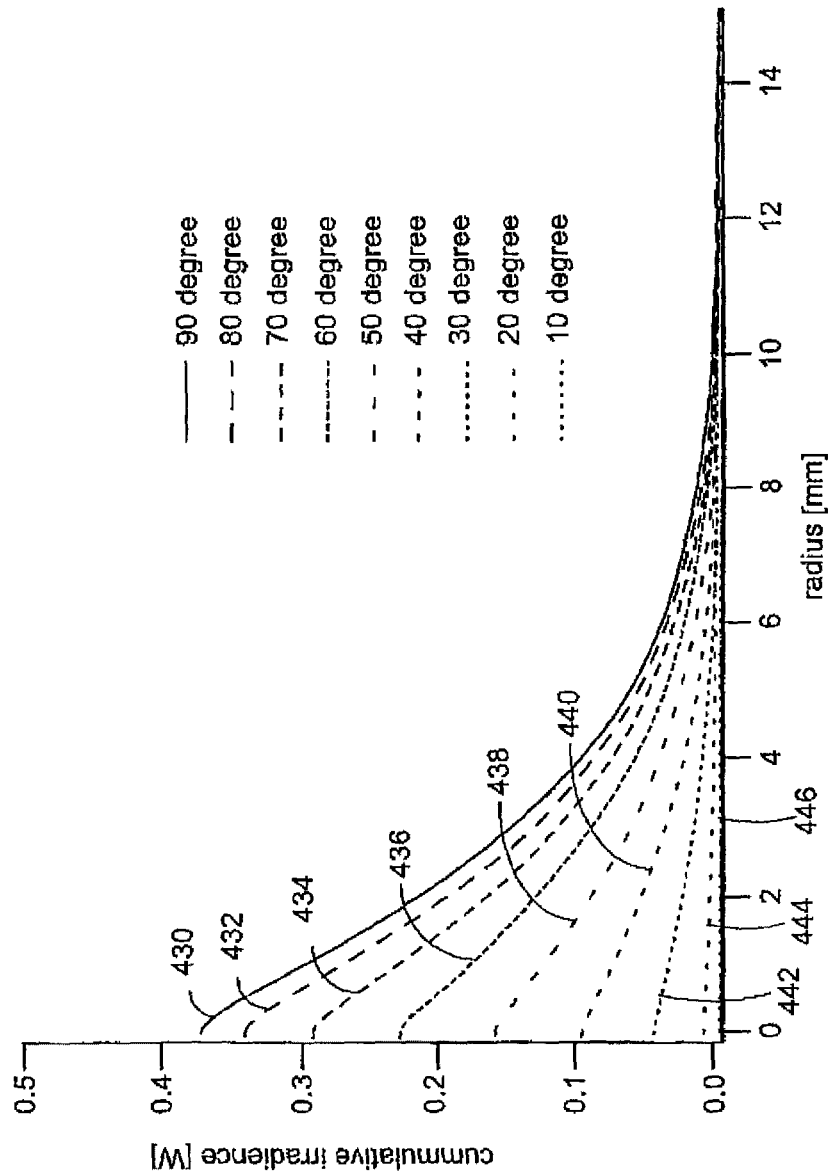

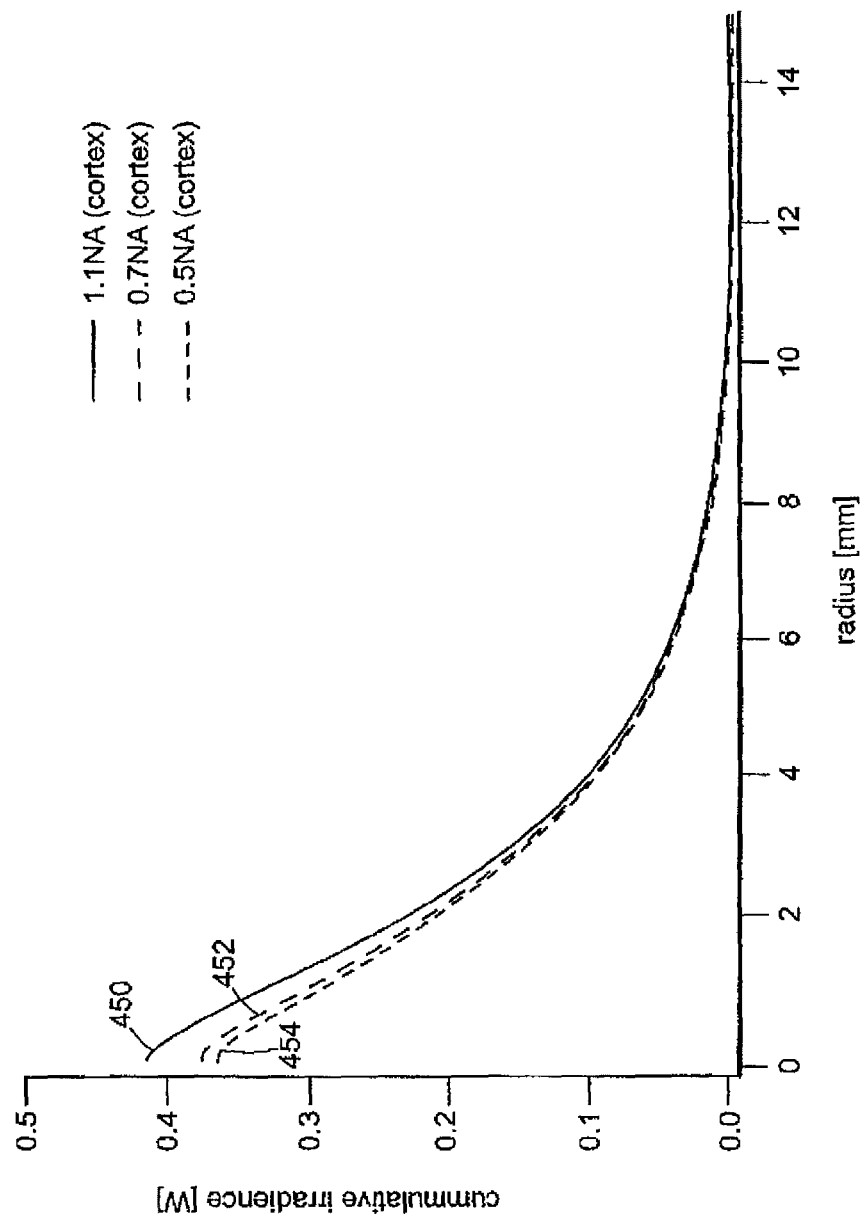

SRS 2845 cm$^{-1}$

SRS 3250 cm$^{-1}$

CARS 3250 cm$^{-1}$

SRS 2845 cm$^{-1}$

SRS 3250 cm$^{-1}$

SRS 2950 cm$^{-1}$

SRS 2950 cm$^{-1}$

SRS 2950 cm$^{-1}$

SRS 2120 cm$^{-1}$

SYSTEMS AND METHODS PROVIDING EFFICIENT DETECTION OF BACK-SCATTERED ILLUMINATION IN MODULATION TRANSFER MICROSCOPY OR MICRO-SPECTROSCOPY

PRIORITY

This application is a continuation of PCT Application Serial No. PCT/US2010/054925, filed on Nov. 1, 2010, that claims priority to U.S. Provisional Patent Application Ser. No. 61/362,003 filed Jul. 7, 2010 and U.S. Provisional Patent Application Ser. No. 61/357,356 filed Jun. 22, 2010, the disclosures of which are hereby incorporated by reference in their entireties.

GOVERNMENT SPONSORSHIP

This application was sponsored by the United States government under National Institutes of Health grant number 1R01EB010244, and the United States government has certain rights to this invention.

BACKGROUND

The invention generally relates to label-free imaging systems, and relates in particular to label-free microscopy and micro-spectroscopy imaging systems employing efficient detection of signals of interest in non-linear optical microscopy and micro-spectroscopy imaging systems and methods.

Conventional label-free optical imaging techniques include, for example, infrared microscopy, Raman microscopy, coherent anti-Stokes Raman scattering (CARS) microscopy and modulation transfer microscopy. Micro-spectroscopy generally involves capturing a spectrum from a microscopic volume in a sample, while microscopy generally involves capturing an image as well as scanning such that multiple images are captured to form picture elements (pixels) of a microscopy image.

Infrared microscopy involves directly measuring the absorption of vibrational excited states in a sample, but such infrared microscopy is generally limited by poor spatial resolution due to the long wavelength of infrared light, as well as by a low penetration depth due to a strong infrared light absorption by the water in biological samples.

Raman microscopy records the spontaneous inelastic Raman scattering upon a single (ultraviolet, visible or near infrared) continuous wave (CW) laser excitation. Raman microscopy has improved optical resolution and penetration depth as compared to infrared microscopy, but the sensitivity of Raman microscopy is rather poor because of the very low spontaneous Raman scattering efficiency (a Raman scattering cross section is typically on the order of $10^{-30}$ cm$^2$). Although spontaneous Raman emissions is emitted in all directions, the low spontaneous Raman scattering efficiency results in long averaging times per image, which limits the biomedical application of Raman microscopy.

FIG. 1A, for example, shows the generation of incoherent emission 10 in a microscopy imaging system that is emitted in all directions from a focal volume 12 after one or more excitation fields are directed toward the focal volume 12 through an objective lens 14. Such a microscopy imaging system may employ one or two-photon excited fluorescence as well as spontaneous Raman emission. As may be seen in FIG. 1A, the emission is produced in the forward as well as the reverse (epi) direction.

CARS microscopy, which uses two pulsed laser excitation beams (pump and Stokes beams), significantly increases the absolute scattering signal due to the coherent excitation. The CARS process, however, also excites a high level of background from the vibrationally non-resonant specimen. Such a non-resonant background not only distorts the CARS spectrum of the resonant signal from dilute sample but also carries the laser noise, significantly limiting the application of CARS microscopy on both spectroscopy and sensitivity perspectives.

One approach to reduce the non-resonant background field in CARS microscopy is to take advantage of the fact that the non-resonant background has different polarization properties than the resonant signal. For example, U.S. Pat. No. 6,798,507 discloses a system in which the pump and Stokes beams are properly polarized and a polarization sensitive detector is employed. Another approach to reducing the non-resonant background field involves detecting the anti-Stokes field in a reverse direction. U.S. Pat. No. 6,809,814 discloses a system in which a CARS signal is received in the reverse direction (epi-direction) from the sample. For transparent samples, however the epi directed signal is significantly smaller than the forward directed signal.

FIG. 1B shows the generation of a signal of interest of a coherent emission microscopy system, such as CARS, second harmonic generation SHG or third harmonic generation THG. The coherent emission 20 in such a microscopy imaging system is emitted primarily in the forward direction as shown at 22, while a much lesser intensity is directed in the reverse (epi) direction as shown at 24 from a focal volume 26 after one or more excitation fields are directed toward the focal volume 26 through an objective lens 28.

Modulation transfer microscopy and micro-spectroscopy imaging systems such as stimulated Raman scattering, stimulated emission, one photon and two photon photo-thermal imaging, two-color two-color absorption, stimulated Brillouin scattering and cross-phase modulation imaging generally involve reliance on the non-linear interaction of two laser beams within a sample, and detection of a characteristic, such as gain or loss, of one of the excitation beams. This is in contrast to detecting a newly generated (new frequency) emission signal as is done, for example, in one-photon and two-photon excited fluorescence, spontaneous Raman scattering, coherent anti-Stokes Raman scattering (CARS), second harmonic generation, (SHG) and third harmonic generation (THG).

Such modulation transfer microscopy and micro-spectroscopy techniques require a detection scheme that provides for detection of a relatively small signal (e.g., a small gain and loss signal) on top of noisy lasers. This is generally achieved based on modulation transfer, that is by modulating a feature of one of the laser excitation beams and measuring the signal of interest with high sensitivity. In particular, the modulation transfers to the other excitation beam due to non-linear interaction within the sample, which facilitates detection of the signal of interest using a modulation sensitive detector. If the modulation frequency is chosen to be faster than the laser noise (e.g., greater than about 200 kHz), shot-noise limited sensitivity may be achieved. Such modulation schemes are readily compatible with beam-scanning microscopy and micro-endoscopy, video-rate imaging speeds, and multiplex excitation schemes.

FIG. 1C shows the generation of a signal of interest of a modulation transfer microscopy or spectroscopy imaging system, such as stimulated Raman scattering, stimulated emission, one photon and two photon photo-thermal imaging, two-color two-color absorption, stimulated Brillouin scattering and cross-phase modulation imaging. One or more excitation fields are directed toward the focal volume 34 through an objective lens 36. As in modulation transfer microscopy, gain or loss of the excitation beams is detected, the emission is effectively only directed into the forward direction. The modulation transfer emission 30 in such a microscopy imaging system is emitted from a focal volume 34 therefore only in the forward direction as shown at 32.

While modulation transfer microscopy and spectroscopy provides high sensitivity in a forward direction, certain applications would benefit from the ability to detect a modulation transfer signal (shown at 30 in FIG. 1C) in the epi direction. Incoherent emission (shown at 10 in FIG. 1A) and to a lesser extent, coherent emission (shown at 20 in FIG. 1B) provide epi-directed emission signals from the focal volume, but have other limitations as discussed above.

There remains a need, therefore, for a microscopy and micro-spectroscopy imaging systems that provide high sensitivity in the epi direction. There is further a need to provide images at a sufficiently high rate that video imaging may be provided. CARS microscopy in certain applications, however, suffers from spectral distortion, limited sensitivity due to unwanted non-resonant background as discussed above, non-linear concentration dependence and coherent image artifacts, thereby limiting quantitative interpretation at video-rate speeds.

SUMMARY

In accordance with an embodiment, the invention provides a microscopy or micro-spectroscopy system that includes a first light source, a second light source, a modulator, an optical assembly and a processor. The first light source is for providing a first illumination field at a first optical frequency $\omega_1$ and the second light source is for providing a second illumination field at a second optical frequency $\omega_2$. The modulator is for modulating a property of the second illumination field at a modulation frequency f of at least 100 kHz to provide a modulated second illumination field. The optical assembly includes focusing optics and an optical detector system. The focusing optics is for directing and focusing the first illumination field and the modulated second illumination field through an objective lens toward the common focal volume along an excitation path. The optical detector system includes at least one optical detector for detecting a detected first field intensity of the first illumination field that is back-scattered within a sample, wherein the optical detector provides an electrical signal representative of the detected first field intensity. The optical detector is located proximate a portion of the excitation path. The processor is for detecting a modulation at the frequency f of the electrical signal due to non-linear optical interaction within the common focal volume.

In accordance with another embodiment, the invention provides a method of performing microscopy or micro-spectroscopy that includes the steps of providing a first illumination field at a first optical frequency providing a second illumination field at a second optical frequency $\omega_2$, modulating a property of the second illumination field at a modulation frequency f of at least 100 kHz to provide a modulated second illumination field, directing and focusing the first illumination field and the modulated second illumination field through an objective lens toward the common focal volume along an excitation path, detecting a detected first field intensity of the first illumination field that is back-scattered within a sample at an optical detector system that includes at least one optical detector, wherein the optical detector is positioned proximate a portion of the excitation path, providing an electrical signal representative of the detected first field intensity; and processing the electrical signal to detect a modulation at the frequency f of the electrical signal due to non-linear optical interaction within the common focal volume.

BRIEF DESCRIPTION OF THE DRAWINGS

The following description may be further understood with reference to the accompanying drawings in which:

FIGS. 1A-1C show illustrative diagrammatic views of a emission patterns during different imaging techniques of the prior art;

FIGS. 5A-5D show illustrative diagrammatic views of optical assemblies for use in modulation transfer microscopy and micro-spectroscopy systems in accordance with different embodiments of the present invention;

FIGS. 9A and 98B show illustrative diagrammatic views of a scanning optical detector system for use in a modulation transfer microscopy or micro-spectroscopy systems in accordance with different embodiments of the present invention employing an x and y scanner motors;

FIGS. 10A and 10B show illustrative diagrammatic views of a scanning optical detector system for use in a modulation transfer microscopy or micro-spectroscopy systems in accordance with different embodiments of the present invention employing a single micro-electro-mechanical (MEMS) element;

FIGS. 11A and 11B show illustrative diagrammatic views of a scanning optical detector system for use in a modulation transfer microscopy or micro-spectroscopy systems in accordance with different embodiments of the present invention employing an scanning fiber endoscope;

FIGS. 16A-16D show illustrative graphical representations of modulation transfer microscopy signal collection intensities under varying optical conditions;

The drawings are shown for illustrative purposes only.

DETAILED DESCRIPTION

The invention provides that modulation transfer microscopy and spectroscopy may be used together with an epi detection technique in accordance with the invention, that provides for efficient collection of the modulation transfer signal from within a sample.

A challenge with epi detection of a modulation transfer signal is that the signal of interest is at the same frequency as one of the excitation fields. While a beam splitter may be used to separate an epi directed modulation transfer signal from the excitation fields along an optical axis of the microscopy system, such a beam splitter will generally lose a significant percentage of the intensity of the modulation transfer signal. Although a different signal path may be employed for the epi directed modulation transfer signal (different than the optical path along with the excitation fields travel to the objective lens), some mechanism must still be employed to either 1) separate the modulation transfer signal from the excitation fields after the modulation transfer signal passes through the objective lens, or 2) to collect the modulation transfer signal through some means other than through the objective lens.

Objective lenses for such modulation transfer microscopy and micro-spectroscopy systems, however, are generally required to provide tight focusing of the excitation fields at the common focal volume in order to generate the required interaction of the fields with the sample. Such objective lenses are therefore, generally rather large and the focal distance is generally rather short, making reception of the modulation transfer signal through the objective lens easier to achieve.

Applicants have discovered that while only a portion of the reflected modulation transfer signal from within the sample is collected by the objective lens through which the excitation fields were delivered to the focal area, a substantial amount of reflected modulation transfer signal may be detected from areas outside of the focal area by employing collection optics that surround the objective lens and/or its optical path.

Modulation Transfer Microscopy and Micro-Spectroscopy Systems

Figure 2:
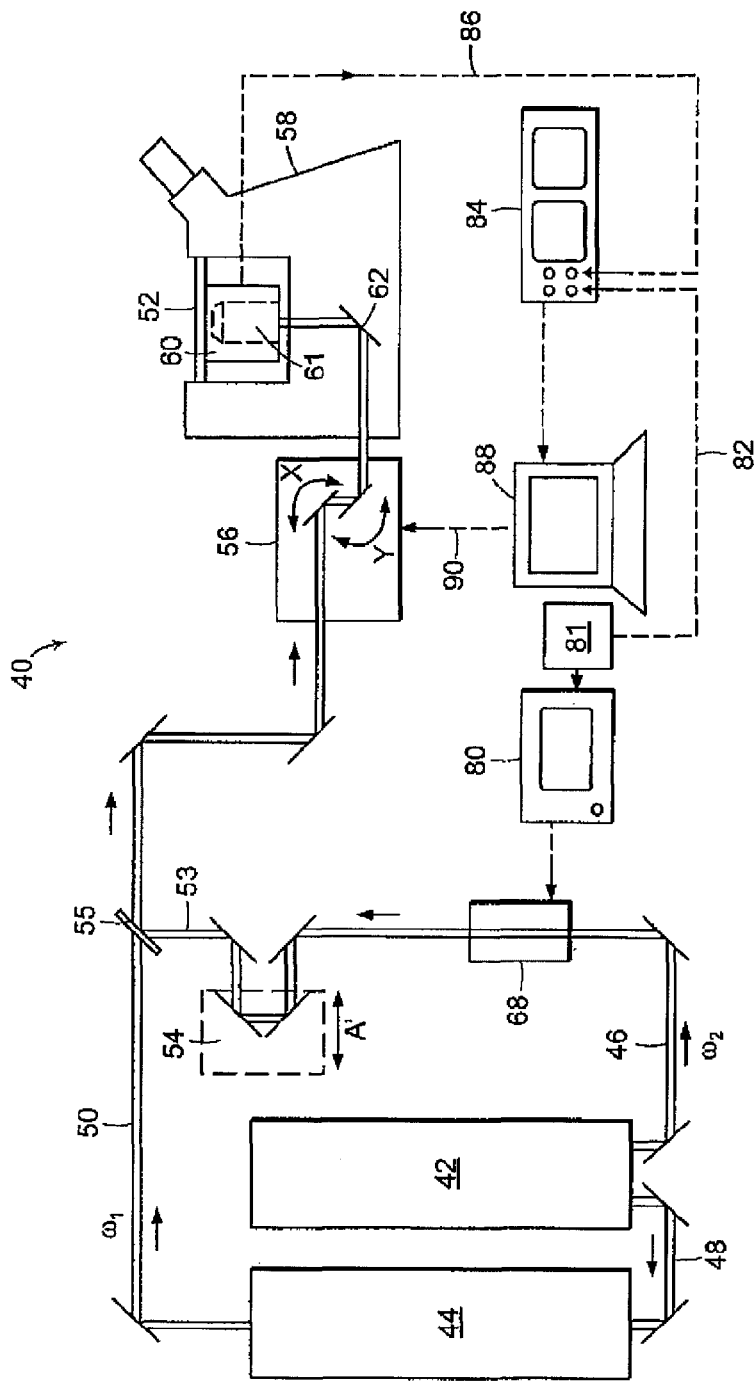
FIG. 2 shows an illustrative diagrammatic view of a modulation transfer microscopy imaging system in accordance with an embodiment of the invention.

FIG. 2, for example, shows a modulation transfer microscopy system in accordance with various embodiments of the invention. Corresponding micro-spectroscopy systems generally involve capturing an image for spectroscopic analysis without scanning the sample. The system may employ a variety of modulation transfer techniques, such as for example, Stimulated Raman Scattering (SRS), SRS Spectral imaging, Stimulated Emission (SE), Ground State Depletion (GD), Photo-Thermal (PT), Two-Color Two-Photon Absorption (TPA), and Stimulated Brillouin Scattering.

Stimulated Raman Scattering (SRS)

In accordance with a certain embodiments, the system 40 includes a dual frequency laser source 42 and an optical parametric oscillator 44 to provide SRS modulation transfer microscopy or micro-spectroscopy. The dual frequency laser source 42 provides a train of laser pulses 46 at a center frequency $\omega_1$ (e.g., a Stokes frequency of about 1064 nm), and a train of laser pulses 48 at a different center frequency (e.g., 532 nm) to the optical parametric oscillator 44. The optical parametric oscillator may be, for example, as disclosed in U.S. Patent Application Publication No. 2008/0037595, the disclosure of which is hereby incorporated by reference in its entirety. The output of the optical parametric oscillator provides a train of laser pulses 50 at a center frequency $\omega_2$ (e.g., a pump frequency) that is selected such that a difference between $\omega_1$ and $\omega_2$ (e.g., $\omega_p - \omega_s$) is resonant with a vibrational frequency of a sample 52 in a focal volume. The train of laser pulses 46 at a center Stokes frequency is modulated by a modulation system, and is then adjusted at a translation stage 54 (that is adjustable as indicated at A) to ensure that the resulting train of laser pulses 53 and the train of laser pulses 50 at the center pump frequency are temporally overlapped. The two trains of laser pulses 53 and 50 are combined at a combiner 55 such that they are collinear and spatially overlapped as well.

The combined trains of laser pulses 53 and 50 are directed via a scan-head 56 (that scans in mutually orthogonal x and y directions), into a microscope 58 that includes an optical assembly 60 that includes an objective lens 61 that directs and focuses the combined trains of laser pulses 53 and 50 into the focal volume, e.g., via a mirror 62. As will be discussed below in further detail with reference to FIGS. 5A-5D, the optical assembly 60 is also provided with a detection system that detects back-scattered and reflected illumination from within the sample, as well as a filter for removing the modulated beam $\omega_2$ (e.g., the Stokes beam). The detection system includes an optical detector that surrounds the objective lens and collects the integrated intensity of substantially all optical frequency components of the other beam $\omega_1$ (e.g., the pump beam) in accordance with an embodiment. The optical detector provides a detection signal 86 to a pixel image processor device 84.

The train of laser pulses 53 is modulated at a modulation frequency f, by a modulation system that includes, for example, a modulator 68, a controller 80, and a modulation source 81. The modulation source 81 provides a common modulation control signal 82 to the controller 80 as well as to a signal processor 84. The integrated intensity of substantially all frequency components of the first pulse train 86 from the optical detector is provided to the signal processor 84, and the modulation (amplitude and/or phase) of the integrated intensity of substantially all the optical frequency components of the train of laser pulses 50 due to the non-linear interaction of the train of laser pulses 53 with the train of laser pulses 50 in the focal volume is detected at the modulation frequency f to provide a pixel of an image to a microscopy control computer 88. The microscopy control computer 88 is employed as an imaging system, and further provides user control of the scan-head 56 as shown at 90.

In accordance with an embodiment, the modulation system may provide amplitude modulation of the $\omega_2$ beam to provide a modulated $\omega_2$ pulse train 23 such that, for example, only alternating pulses (or one of every n pulses) of the $\omega_2$ pulse train (46 shown in FIG. 2) are coincident with the pulses of the $\omega_1$ pulse train 50 and/or provide a difference frequency that is resonant with the molecular vibration of a molecule in focal area. Amplitude modulation of the $\omega_2$ beam may be achieved using a Pockel cell and a polarization analyzer as the modulator 68, and a Pockel cell driver as the controller 80. In accordance with this embodiment, the modulation rate is half the repetition rate of the laser such that every other pulse of the original $\omega_2$ pulse train is reduced in amplitude to provide that stimulated Raman scattering does not substantially occur in the focal volume with the pulses having the reduced amplitude. If the modulation rate is of the same order of the repetition rate of the laser, countdown electronics must be utilized to guarantee the synchronization (phase) between the modulation and the pulse train. A wide variety of different modulation rates are also possible. In further embodiments, the contrast pulses may have an amplitude that is substantially zero by switching off the pulses at the modulation frequency, for example using an electro-optic modulator (such as a MEMs device or a galvanometric scanner) or an acousto-optic modulator.

Amplitude modulation of the pump or Stokes pulse trains may therefore be achieved, and the increase of the Stokes pulse train or decrease of the pump pulse train may be determined using a lock-in amplifier. The modulation may be provided using a Pockel Cell and a polarization analyzer. By modulating the pump train of pulses and then detecting the Stokes train of pulses from the focal volume, Raman gain may be determined by the processing system. In further embodiments, the Stokes beam may be modulated, the pump beam may be detected from the focal volume, and Raman loss may be determined by the processing system.

The system of the above embodiment of the invention therefore, provides that stimulated Raman scattering microscopy may be achieved using a modulation of one of the pump or Stokes beams as a contrast mechanism. Stimulated Raman scattering microscopy bears several advantages. In particular: (1) it is an optically stimulated process that significantly enhances the molecular vibrational transition efficiency compared to conventional Raman microscopy, which relies on spontaneous scattering; (2) it is a nonlinear process in which the signal is only generated at the microscopy objective focus, rendering a three-dimensional sectioning ability; (3) it only probes the vibrational resonance, and is therefore free from interference with the non-resonant background (unlike in the CARS microscopy where non-resonant background is always present); (4) the signal always scales linearly with the solute concentration, allowing ready analytical quantification; (5) the signal may be free from sample auto-fluorescence; (6) the phase matching condition is satisfied for any relative orientations of the beams (unlike in the CARS microscopy); (7) visible and near-IR beams are used resulting in a higher penetration depth and spatial resolution than IR absorption microscopy; and (8) the detection of Raman gain or loss is also unaffected by ambient light, which permits such systems to be used in open environments. Further details regarding the operation and structure of various embodiments of systems and methods of such a technique to provide Simulated Raman Scattering are disclosed in U.S. Published Patent Application Publication No. 2010/0046039, the disclosure of which is hereby incorporated by reference in its entirety.

The process may be viewed as a two photon process for excitation of a vibrational transition. The joint action of one photon annihilated from the pump beam and one photon created to the Stokes beam promotes the creation of the molecular vibrational phonon. The energy of the pump photon is precisely converted to the sum of the energy of the Stokes photon and the molecular vibrational phonon. As in any two photon optical process, the transition rate is proportional to the product of the pump beam intensity and the Stokes beam intensity. A molecular vibrational level is necessary for this process to happen, as required by the energy conservation. There is, therefore, no contribution from non-resonant background.

For stimulated Raman loss of the pump beam, this third-order non-linear induced polarization radiates at the pump beam frequency. The intensity dependence of this nonlinear radiation scales linearly with pump beam and quadratically with Stokes beam. Its final phase is 180 degree lag behind that of the input pump beam at the far field detector. The interference therefore, between this non-linear radiation and input pump beam results in an attenuation of the pump beam itself. The intensity dependence of the interference term also scales linearly with both the pump beam and Stokes beam.

For stimulated Raman gain for Stokes beam, a different third-order nonlinear induced polarization radiates at the Stokes beam frequency. The intensity dependence of this nonlinear radiation scales quadratically with pump beam and linearly with Stokes beam. Its final phase is the same as that of the input Stokes beam at the far field detector. The interference therefore, between this nonlinear radiation and input Stokes beam results in an increase of the Stokes beam itself. The intensity dependence of the interference term again scales linearly with both the pump beam and Stokes beam.

Although the use of amplitude modulation has the highest modulation depth, this approach may introduce a linear background due to a modulation of the temperature or refractive index of the sample due to the intensity modulation on the sample. In accordance with another embodiment, the modulation system may provide polarization modulation as disclosed in U.S. Published Patent Application Publication No. 2010/0046039, and may include a polarization device as the modulator 68, and a polarization controller as the controller 80. Every other pulse of the $\omega_2$ pulse train has a polarization that is different than that of the other preceding pulse. In this embodiment, each of the $\omega_2$ pulses of the pulse train 53 is coincident with a $\omega_1$ pulse of the $\omega_1$ pulse train 50. Different modulation rates other than half of the repetition rate of the laser (in which every other pulse is different) can also be applied if synchronization of the modulation and the pulse train is insured electronically.

Polarization modulation also provides that stimulated Raman scattering does not substantially occur in the focal volume with the pulses having the altered unparallel polarization. In certain embodiments, the modulator includes a polarization filter to remove one of the sets of pulses as a further contrast mechanism. The polarization of the pulses may therefore, be modulated with respect to each other. In other embodiments, the detector itself may distinguish between the modulated pulses. In particular, when pump and Stokes pulse trains are perpendicular to each other, a different tensor element of the non-linear susceptibility is probed compared to the case where pump and Stokes field are parallel. Different tensor elements have significantly different magnitudes; this converts the polarization modulation of the excitation beams into amplitude modulations of the gain/loss signal; which may then be detected with the lock-in amplifier. Polarization modulation may be implemented with a Pockel cell. This approach has the advantage that it does not introduce a temperature modulation of the sample.

In accordance with other embodiments, one of the pulse trains may be modulated by time (or phase)-shifting. For example, the modulated $\omega_2$ pulse train 53 may include alternating pulses, e.g., only every other of which coincides with a $\omega_1$ pulse, while the remaining pulses are time shifted such that they do not coincide with a $\omega_1$ pulse. This provides a contrast mechanism on the basis of which signal of interest may later be extracted.

Modulation of one or both of the pump and Stokes beams may also be achieved by frequency modulation as disclosed, for example, in U.S. Pat. No. 7,352,458, the disclosure of which is hereby incorporated by reference in its entirety. In a frequency modulation system, the frequency of one or both of the pump and Stokes beams is alternately modulated at a modulation frequency such that a difference frequency between the pump and Stokes beams (e.g., $\omega_p-\omega_S$) is tuned in and out of a vibrational frequency of the sample. The detector then detects the gain/loss that is generated through non-linear interaction of $\omega_p$ and $\omega_S$ and the sample responsive to the modulation frequency. An output signal may be passed through a lock-in amplifier such that only changes at the time scale of the modulation period are provided in the final output. In accordance with further embodiments, other modulation schemes may be employed such as time-delay modulation, spatial beam mode modulation, etc., which will each introduce a modulation of a generated signal. In such a frequency modulation system, the $\omega_2$ pulse train is modulated such that the pulses alternate between frequencies of $\omega_2$ and $\omega_2'$. While the difference frequency of $\omega_2-\omega_1$ yields high Raman intensity at resonance with a sample, the modified difference frequency of $\omega_2'-\omega_1$ yields only a background signal. The detection signal of interest may therefore be readily isolated using the frequency responsive detector. Systems for providing frequency modulation of a pulse train may, for example, include an additional optical parametric oscillator again, such as disclosed in U.S. Patent Application Publication No. 2008/0037595, the disclosure of which is hereby incorporated by reference in its entirety.

In accordance with further embodiments, for example, a system of the invention may include a dual frequency laser source, a first optical parametric oscillator, as well as an additional optical parametric oscillator by splitting the power of the original laser source. The dual frequency laser source provides a first train of laser pulses at a center pump frequency, and an intermediate train of laser pulses at a center frequency to the first optical parametric oscillator and to the second optical parametric oscillator. The output of the first optical parametric oscillator provides a first Stokes train of laser pulses at a center Stokes frequency $\omega_2$ that is selected such that a difference between $\omega_1$ and $\omega_2$ (e.g., $\omega_p-\omega_S$) is resonant with a vibrational frequency of a sample (not shown) in a focal volume. The output of the optical parametric oscillator provides a second Stokes train of laser pulses at a center frequency $\omega_2'$ that is selected such that a difference between $\omega_1$ and $\omega_2'$ (e.g., $\omega_p-\omega_S'$) is not resonant with a vibrational frequency of the sample in the focal volume.

The $\omega_2'$ pulses are passed through a half wave plate and combined with the $\omega_2$ pulses that are passed through a different half wave plate. The half wave plates ensure that the pulse trains have different polarization such that one is transmitted by the beam splitter and the other is reflected. The combined pulse train thereby includes both the $\omega_2$ and the $\omega_2'$ pulses, wherein the $\omega_2$ and the $\omega_2'$ pulses include mutually orthogonal polarizations. The combined $\omega_2$ and the $\omega_2'$ pulses are passed through a modulator that applies a modulation frequency f from a modulation source responsive to a modulation signal. The modulator (together with a polarization analyzer) alternately selects, at the modulation rate f, $\omega_2$ or $\omega_2'$, pulses based on the polarization. The result, may be, for example, that a pulse train of alternating $\omega_2$ and $\omega_2'$ pulses is provided, or that one $\omega_2$ pulse is provided for every two or more $\omega_2'$ pulses. The train of $\omega_1$ laser pulses may be temporally adjusted at a translation stage to ensure that the train of $\omega_1$ laser pulses and the train of modulated $\omega_2$ laser pulses are temporally overlapped. The two trains of laser pulses are combined at a combiner such that they are collinear and spatially overlapped as well.

The combined trains of $\omega_1$ and modulated $\omega_2$ laser pulses are directed via a scan-head into a microscope that includes optics that direct and focus the combined trains of $\omega_1$ and modulated $\omega_2$ laser pulses onto a sample 52 in the focal volume as discussed above. A resulting back-scattered and reflected illumination is directed onto an optical detector, and is filtered by a filter to yield only the $\omega_1$ pulse train, which is detected by an optical detector, such as a photodiode as discussed further below with reference to FIGS. 5A-5D.

A signal representing the integrated intensity of substantially all frequency components of the first pulse train from the optical detector is provided to the signal processor, and the modulation (amplitude and/or phase) of the integrated intensity of substantially all the optical frequency components of the train of laser pulses due to the non-linear interaction of the first train of laser pulses with the modulated second train of laser pulses in the focal volume is detected at the modulation frequency f to provide a pixel of an image to a microscopy control computer. The modulation transfer from the second train of pulses to the first train of pulses is therefore employed as a contrast mechanism for the microscopy technique. The microscopy control computer is employed as an imaging system, and further provides user control of the scan-head as discussed above to provide a microscopy imaging system in accordance with an embodiment.

In accordance with further embodiments, the system may include an electronically locked laser such as an electronically locked titanium sapphire laser in place of the optical parametric oscillator. In further embodiments, the system may include a single optical parametric oscillator that provides both the $\omega_2$ pulses and the $\omega_2'$ pulses. In still further embodiments, both pulse trains may be provided by a dual frequency laser source system as disclosed in U.S. Provisional Patent Application Ser. No. 61/357,328 filed on even date herewith, the disclosure of which is hereby incorporated by reference in its entirety; such a dual frequency laser source system, for example, may employ a mode-locked laser and a fiber laser system comprising a continuous wave single pass laser, the output of which is spectrally phase-modulated, then modulated to provide chirped pulses that are then temporally compressed to provide a train of pulses that are synchronous with pulses from the mode-locked laser.

If a single modulation is not sufficient to suppress the laser noise completely, two independent modulations may be combined; two detection schemes are therefore possible, e.g., double-modulation and inter-modulation. With double-modulation, a first modulation is done at a higher frequency than the second and is demodulated by the first lock-in detector with a time constant that will allow passing the modulation at the second rate. The demodulated signal from the first lock-in amplifier will therefore still possess the second modulation that is demodulated with a second lock-in amplifier. With inter-modulation, two independent modulations have similar rates and the signal is detected at the sum or difference frequency of the modulation rates with a single lock-in amplifier. A system such as a Stanford Research SR844FM lock-in amplifier, ConOptics 360-80 Pockel cell may be used to achieve this.

The realization of Raman gain/loss microscopy relies on the right combination of the excitation laser source, signal detection based phase-sensitive detection and laser scanning microscopy. Again, the signal is generated if two pulse trains of frequency $\omega_p$ (pump beam) and $\omega_S$ (Stokes beam) interact in the sample and $\Delta\omega=\omega_S-\omega_p$ equals the frequency of a molecular vibration of the molecule in focal volume. Due to the non-linear optical interaction, the pump beam is depleted and the Stokes beam is increased. Which molecular species is detected is chosen prior to the imaging by tuning $\Delta\omega$ into the Raman resonance of the molecule of interest. Thus Raman Gain/Loss measurements require two overlapped lasers beams, ideally with tunable wavelength to address different $\Delta\omega$. Pulsed lasers with higher peak field strengths increase the size of the signal and thus lower the pixel dwell time. The signal is a small decrease (Raman Loss)/increase (Raman Gain) of the intensity of the pump/Stokes beam and as such sits on the background of the intensities of the excitation beams. It can be separated from this background by amplitude modulation and phase-sensitive detection. This allows the determination of the concentration of the vibrationally resonant molecule species in the focal spot. By scanning the focal spot through the sample, i.e., in a beam scanning microscope, a 3-dimensional image of the distribution of the selected molecular specimen can acquired.

The choice of laser pulse width is critical in this non-linear microscopy. The signal depends non-linearly on the excitation intensities as it is proportional to the product $I_{Pump} \cdot I_{Strokes}$, where $I_{Pump}$ and $I_{Strokes}$ are the intensities of the pump and Stokes beam respectively. As such the signal may be increased by using pulsed lasers with high peak intensities of $I_{Pump}$ and $I_{Stokes}$ but the same average intensity on the sample. The pulse-width of the laser-pulse $\Delta t$ and its bandwidth in frequencies $\Delta\omega$ however, are related by the equation $\Delta t \cdot \Delta\omega = \text{const}$. So in order to produce a short pulse one requires a spectrally broad pulse. The typical line-width of a Raman band is ~10-15 $cm^{-1}$ which corresponds to a pulse-width of ~2-3 ps if the laser bandwidth is chosen to match the line-width of the Raman band. Utilizing a longer pulse-width will sacrifice the peak intensities and therefore decrease the non-linear signal. Utilizing a shorter pulse-width with a greater number of contributing frequencies will not increase the signal further as most of the excitation is off vibrational resonance. This unnecessarily increases the power on the sample and thus the photo-damage. Thus the use of laser with a typical pulse-width of several ps is ideal. For this pulse-width a repetition rate of ~80 MHz is ideal to decrease photo-damage of the sample. In order to focus into the same spot which is necessary to generate the signal (spatial overlap) the beams have to be parallel and of same divergence. When pulsed lasers are used, the pulses have to occur at the same time (temporally overlap), i.e., the repetition rate of the two beams has to be equal and the time delay has to be adjustable to overlap the pulsed or intrinsically zero.

At least one of the pump or Stokes pulses may have tunable wavelength to allow the choice or scanning of a Raman band, i.e., a molecular species. The wavelength should be adjustable to at least ~0.1 nm precision as Raman bands have a typical width of ~0.5 nm. The use of lasers in the near IR (700 nm-1500 nm) has advantages for biomedical imaging as penetration depth is maximized and photo-damage is minimized due to minimal absorption and scattering at these wavelengths. Thus there is no limitation to use the technique in vivo or on human patients. In some occasions of the use of visible and UV lasers may be useful to boost the signal (through electronic enhancement), sacrificing the advantages of penetration depth and photo-damage with near IR sources.

In certain applications, a combination of a synchronously pumped OPO and a pump-laser may be used, and saturable absorbers may be used to tune the pulse-width (SEASAM technology). Typical gain media generate light at 1064 nm which can then be frequency doubled to 532 nm to pump an OPO generating a signal beam at 700 nm-1000 nm and an idler beam at 1100 nm-2000 nm. Either signal and/or idler beam can be used (signal+idler) or they can be combined with some of the 1064 nm light that has not been frequency doubled respectively (signal +1064 nm or idler +1064 nm). Due to the synchronous pumping, the repetition rate is matched automatically. Signal and idler beam are overlapped in time intrinsically and the time delay between the signal/idler and the 1064 nm output can be achieved with a delay stage. Alternatively synchronized Ti:Sa laser or fiber-lasers can be used. A commercially available system such as a High Q Picotrain+APE Berlin Emerald OPO may be used.

Because Raman Gain/Loss results in an increase/depletion of the excitation beams, the modulation transfer illumination originating from the non-linear optical interaction is directed in the forward direction only. In highly scattering samples as tissue, the forward traveling light is however, back-scattered within the sample. If either one of the excitation beams is further resonant with one photon absorption of the sample, transient absorption is detected. Thus detection is possible and necessary in epi-direction for scattering samples. As such, Raman Gain/Loss microscopy has the potential to be implemented for endoscopic imaging.

Raman Loss microscopy was implemented in a modified Olympus FY-300 microscope using the tunable signal beam (pump beam) from the APE Berlin Emerald OPO and the 1064 nm output (Stokes beam) from the HighQ pump laser. The signal was detected in forward direction with a Thorlabs FDS1010 large area photodiode and the 1064 nm beam was blocked with a Chroma 890/220 band-pass filter after passing through the focus and the sample. Polarization modulation of the Stokes beam with the ConOptics 360-80 Pockel Cell at 1 MHz was used to introduce the amplitude modulation of the signal which was then extracted with a Stanford Research SR844 RE lock-in amplifier. Proper RF-shielding was critical to get rid of RF-pickoff from the high-voltage driving of the Pockel cell.

During the non-linear interaction of the modulated Stokes train of pulses and the pump train of laser pulses when focused through the objective lens, both the pump and Stokes pulses are directed in a forward direction. In accordance with various embodiments one or more detectors may be positioned in the reverse direction generally surrounding the incoming pump and Stokes pulse trains that are directed into the focal volume. In such as reverse direction detection system, the detector will detect reflected pump pulses from outside of the focal volume.

Figure 3:
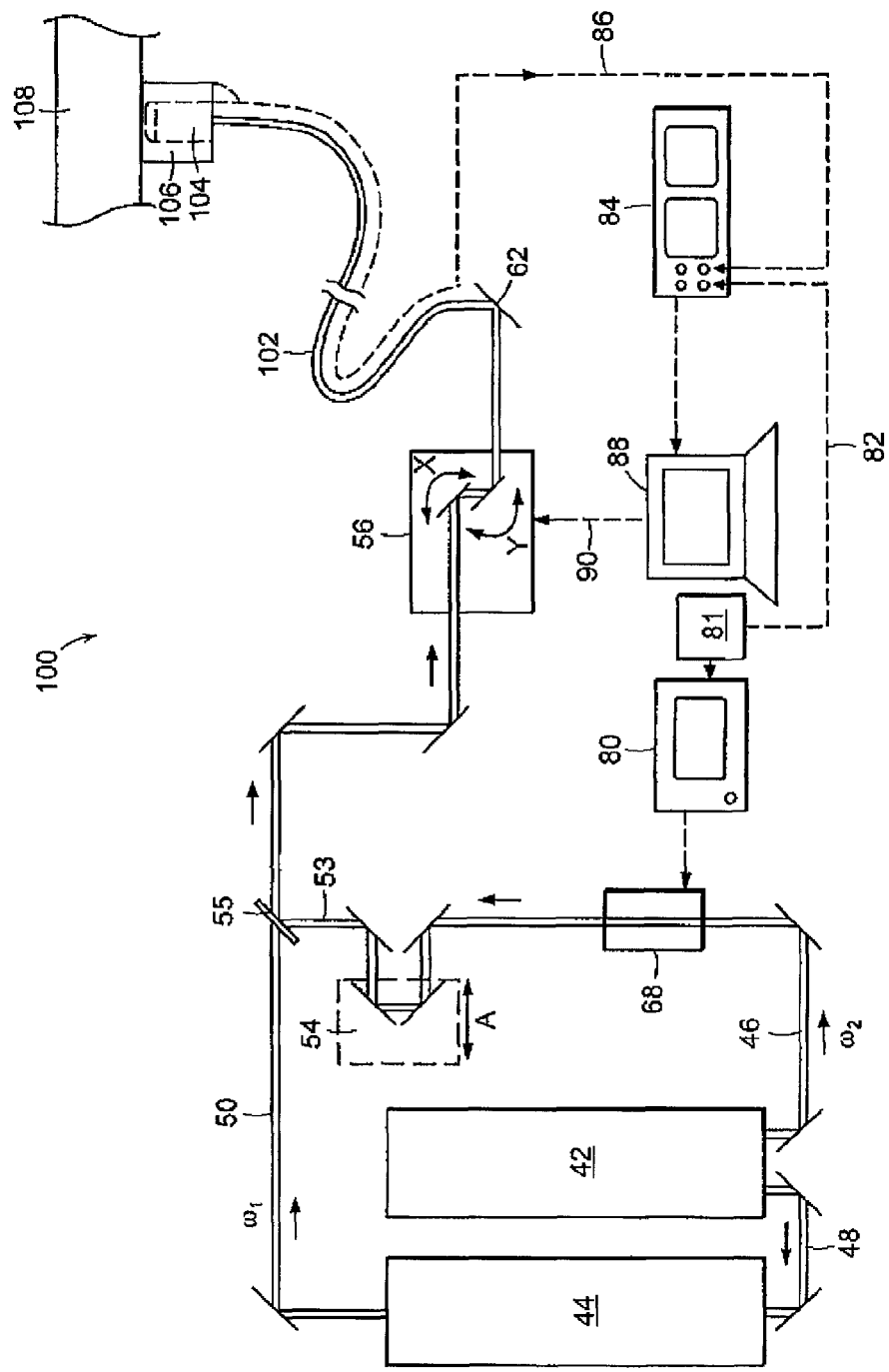
FIG. 3 shows an illustrative diagrammatic view of a modulation transfer microscopy imaging system in accordance with another embodiment of the invention.

FIG. 3 shows a system 100 that includes the same elements as shown in FIG. 2 that include the same reference numerals as the system 40 of FIG. 2, except in the system 100, the combined trains of laser pulses 53 and 50 are directed into an optical fiber 102 and then through an objective lens 104 of an optical assembly 106. The objective lens 104 directs and focuses the combined trains of laser pulses 53 and 50 into a focal volume within a thick sample 108. Again, as will be discussed below in further detail with reference to FIGS. 5A-5D, the optical assembly 106 is also provided with an optical detector system that includes an optical detector that detects back-scattered and reflected illumination from within the sample, as well as a filter for removing the modulated beam $\omega_2$ (e.g., the Stokes beam). The optical detector system includes one or more optical detectors that generally surround the objective lens and collects the integrated intensity of substantially all optical frequency components of the other beam $\omega_1$ (e.g., the pump beam) in accordance with an embodiment. The optical detector provides the detection signal 86 to the pixel image processor device.

Figure 4:
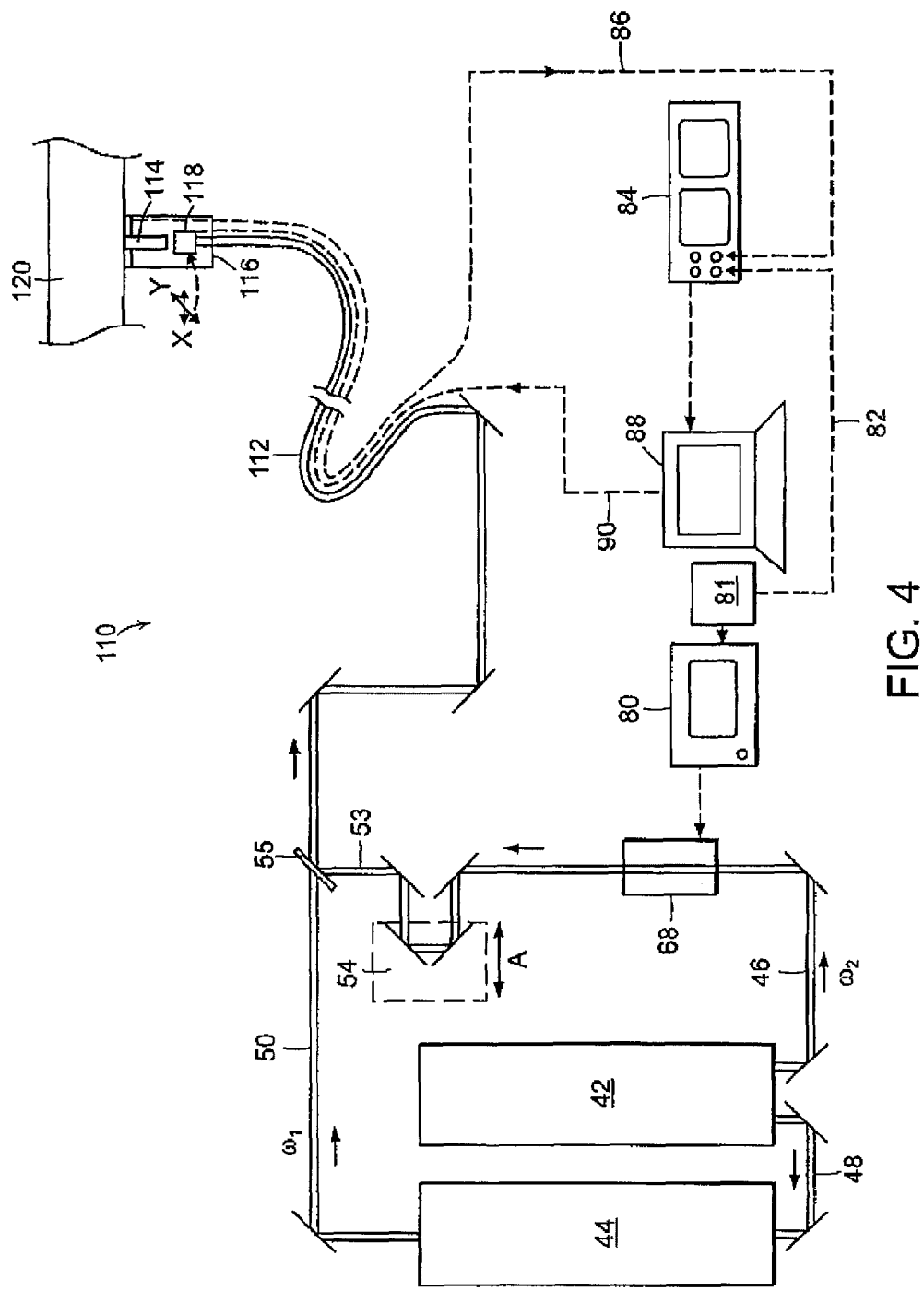
FIG. 4 shows an illustrative diagrammatic view of a modulation transfer microscopy imaging system in accordance with a further embodiment of the invention.

FIG. 4 shows a system 110 that also includes the same elements as shown in FIG. 2 that include the same reference numerals as the system 40 of FIG. 2, except in the system 110, the combined trains of laser pulses 53 and 50 are directed into an optical fiber 112 and then through an objective lens 114 of an optical assembly 116 that also includes a scanning assembly 118. The objective lens 114 directs and focuses the combined trains of laser pulses 53 and 50 into a focal volume within a thick sample 120. As will be discussed below in further detail with reference to FIGS. 8A-8B, 9A-9B, 10A-10B and 11A-11B, the optical assembly 116 includes the scanning assembly 118 that provides for x and y direction scanning within the sample 120. The optical assembly 116 is also provided with an optical detector system that includes an optical detector that detects back-scattered and reflected illumination from within the sample, as well as a filter for removing the modulated beam $\omega_2$ (e.g., the Stokes beam). The optical detector system includes one or more optical detectors that generally surround the objective lens and collects the integrated intensity of substantially all optical frequency components of the other beam $\omega_1$ (e.g., the pump beam) in accordance with an embodiment. The optical detector provides the detection signal 86 to the pixel image processor device. In further embodiments, the system 110 may also include both the scanning assembly 118 as well as the scan-head 56 of the system of FIG. 2.

The invention provides, therefore, in accordance with various embodiments, that optical imaging with molecular specificity may be achieved to provide in vivo SRS imaging. This would allow in vivo imaging of water, lipid and protein in skin as well as mapping of penetration pathways of topically-applied drugs in animals and humans.

SRS Spectral Imaging

In accordance with further embodiments and again with reference to FIGS. 2, 3 and 4, the laser source 42 (of FIGS. 2, 3 and 4) may further include a spectral shaper to provide spectral shaping of the train of laser pulses $\omega_2$ as disclosed in U.S. patent application Ser. No. 12/690,579 filed Jan. 20, 2010 to provide SRS Spectral shaping modulation transfer microscopy or micro-spectroscopy. In particular, each pulse of the train of laser pulses to be output by the source 42 is spectrally shaped by a shaping assembly that includes a spectral dispersive element, a lens and a spatial light modulator. The dispersive element spectrally disperses each broadband pulse, and the spatial light modulator then modulates different frequency components of the spectrally disperse broadband pulse to provide a train of shaped pulses 46.

The train of shaped laser pulses 46 is then modulated by the modulator 68, and is then phase adjusted at a translation stage 54 (that is adjustable as indicated at A) to ensure that the resulting train of modulated shaped laser pulses and the train of laser pulses 50 at the center pump frequency are temporally overlapped. The two trains of laser pulses 50 and 53 are combined at the combiner 55 such that they are collinear and spatially overlapped as well. The trains of laser pulses may be provided by laser source systems discussed above with reference to the SRS modulation transfer microscopy and micro-spectroscopy systems.

The combined trains of laser pulses 50, 53 are directed toward the objective lens 61, 104, 114 that directs and focuses the combined trains of laser pulses 50, 53 into the focal volume. The back-scattered and reflected illumination from the non-linear optical interaction within the focal volume is directed onto an optical detector (e.g., one or more photodiodes), and the modulated shaped beam (e.g., the Stokes beam) is blocked by an optical filter, such that the optical detector measures the intensity of the other beam $\omega_1$ (e.g., the pump beam) only.

The train of shaped laser pulses 46 is modulated at modulation frequency f (e.g., at least about 100 kHz), by a modulation system that includes, for example, the modulator 46, a controller 80 and a modulation source 81. The modulation source provides a common modulation control signal to the controller 80 as well as to the detector and to the signal processor 84. The integrated intensity of substantially all frequency components of the first pulse train from the optical detector is provided to the signal processor, and the intensity modulation due to the non-linear interaction of the train of laser pulses with the train of laser pulses in the focal volume is detected at the modulation frequency f to provide a pixel of an image to a microscopy control computer. The microscopy control computer is employed as an imaging system, and further provides user control of the scan-head.

Stimulated Emission (SE) and Ground State Depletion (GD)

In accordance with further embodiments and again with reference to FIGS. 2, 3 and 4, the systems 40, 100 and 110 may provide stimulated emission (SE) or ground state depletion (GD) modulation transfer microscopy or micro-spectroscopy, as these techniques rely on modified transmission properties of the sample for the first beam 53 (probe beam) as a result of excitation by the second beam 50 (pump beam).

In stimulated emission microscopy, the second beam excites molecules in the sample into an excited state, and when these molecules interact with the first beam, they emit light into that beam with matched polarization and phase, increasing the brightness of that beam. In ground state depletion microscopy, the second beam removes molecules from the ground state by promoting them to an excited state. In this case, fewer molecules in the sample are in the ground state, and thus the absorption of the first beam is reduced. In order to modify the populations of molecules in the sample, the beams are typically chosen to match the one or two-photon electronic absorption resonances of the molecule in the ground or excited state. Femtosecond (fs) pulse-width lasers may be used to maximize the signal, and the probe pulse may also be delayed for improving the modulation transfer signal.

For stimulated emission microscopy for example, the emission of non-fluorescent or weakly fluorescent samples are stimulated to an electronic excited state. If the sample is fluorescent, a spontaneous fluorescent emission would occur, bringing the energy level back down to an electronic non-excited state. If the sample is non-fluorescent, a non-radiative decay will occur. The stimulation beam 50 and excitation beam 53 may be provided as synchronized trains of pulses (provided by laser source systems discussed above with reference to the SRS modulation transfer microscopy and micro-spectroscopy systems), and/or may comprise continuous wave (cw) fields at center frequencies $\omega_2$ and $\omega_1$.

Again, with reference to FIGS. 2, 3 and 4, if the systems 40, 100 and 110 are used for stimulated emission or ground state depletion microscopy in accordance with various embodiments of the invention, a laser source system (that may include a laser source 42 and an optical parametric oscillator 44 for providing the excitation beam 53 (e.g., an excitation train of laser pulses) at an excitation center frequency $\omega_1$ and a stimulation beam 50 (e.g., a stimulation train of laser pulses) at a stimulation center frequency $\omega_2$. The laser source system may alternatively include two lasers in other embodiments. The excitation train of pulses is modulated by a modulator 68, and the modulated excitation train of pulses 53 is combined with the stimulation train of pulses 50 at the combiner 55. The delay unit 54 may be provided in the path of either the excitation or stimulation beam prior to the beams being combined to adjust one of the beams with respect to the other.

The modulator 68 may, for example, be an acousto-optic modulator that switches the excitation train of pulses on and off at 5 MHz. The combined modulated excitation train of pulses and stimulation train of pulses 53, 50 are provided to a microscope 58 as discussed above, where the collinear modulated excitation and stimulation beams are focused with a high numerical aperture (N.A.) objective (NA=1.2) onto the common focal spot. The temporal delay between the synchronized excitation and stimulation inter-pulse is adjusted to about 0.2 ps by using a translational stage. The intensity of the excitation beam is modulated by an acousto-optical modulator at 5 MHz. To acquire images with laser beam scanning, a 100 μs time constant maybe used for the lock-in amplifier system together with a pixel dwell time of 190 μs. In certain embodiments, the reflector system 62 may further include x and y direction scanners (such as mirrors or a scanning light modulator) for scanning in x and y directions in a sample 52, 108 and in accordance with the embodiment of FIG. 4, the system 110 includes a scanning assembly 118 for scanning in x and y direction in the sample 120. In other embodiments, a stage on which the sample 52 is placed may be adjustable in x and y directions. In certain embodiments, the objective 61, 104, 114 may permit scanning in the z direction.

As discussed in further detail below with reference to FIGS. 5A-5D, the tightly focused combined modulated excitation train of pulses and stimulation train of pulses is directed toward the sample 52, 108, 120, and reflected modulation transfer illumination from within the sample is collected by optics, a filter and a detector within the optical assembly 60, providing a detection signal 86 to a pixel image processor 84.

A lock-in amplifier system (that includes the controller 80 and a modulation source 81) is coupled to both the modulator and the pixel image processor 84 such that the modulation may be employed by the detection system to identify via image contrast the illumination of interest from filtered modulation transfer illumination. The detector provides the detector signal 86 to the processing unit 84, which provides pixel data for an imaging system.

Each excitation pulse from the modulated train of excitation pulses causes chromophores in the sample to change energy states from the low (or ground) state to the electronic excited state, and a quickly following stimulation pulse from the train of stimulation pulses stimulates emission, causing the energy to be released as illumination at the excitation frequency, increasing the total radiative quantum yield by as much as from $10^{-5}$ to unity. As a result, the originally weakly or non-fluorescent species are turned into highly radiating species. Further details regarding the operation of a stimulated emission system of various embodiments are disclosed in U.S. patent application Ser. No. 12/417,993 filed Apr. 3, 2009, the disclosure of which is hereby incorporated by reference in its entirety.

Photo-Thermal (PT) Imaging

In accordance with further embodiments, the modulation transfer technique may employ one and two color photo-thermal (PT) microscopy. Photo-thermal microscopy relies on modified transmission properties of the sample for a first beam (probe beam) as a result of heating of a sample by the second beam (pump beam), e.g., by thermal lensing or thermal phase shifting. In order to heat the sample volume effectively, the pump beam is typically chosen to match the one or two-photon electronic absorption frequency of the molecule. The probe beam may be either pulsed or continuous wave (cw). In thermal lens microscopy, an aperture is typically used to convert changes in the beam profile as a result of the non-linear interaction into changes in intensity.

Again with reference to FIGS. 2, 3 and 4, if the systems 40, 100 and 110 are used for photo-thermal microscopy, then the system may include a dual frequency source 42 for providing a combined first train of laser pulses (e.g., a pulsed Stokes field) and a second train of laser pulses (e.g., a pulsed pump field). The combined trains of laser pulses are modulated by a modulator 68 at a modulation frequency. Another source 42 provides probe illumination (for example, a train of pulse or a continuous wave (CW) laser output or a high repetition rate laser output (e.g., 1 GHz) having a different frequency) that is combined with the modulated trains of laser pulses at a dichroic mirror 55. The source 42 may or may not receive a train of laser pulses from the dual frequency source 42. The combined modulated trains of laser pulses and the probe illumination are then all provided to an objective lens 61, 104, 114 as discussed above that focuses the beams onto a focal area of a sample 52, 108, 120. The pump beam 50 and probe beam 53 may be provided as synchronized trains of pulses (provided by laser source systems discussed above with reference to the SRS modulation transfer microscopy and micro-spectroscopy systems), and/or the probe beam 53 may comprise continuous wave (cw) fields at a center frequency $\omega_2$.

SRS excitation for this photo-thermal system may be provided by using two pulsed laser beams (one pump beam and one Stokes beam) that are jointly used to stimulate vibrational transitions, which lead to an intensity decrease (stimulated Raman loss) of the pump beam and/or an intensity increase (stimulated Raman gain) of the Stokes beam. High frequency modulation of one of the pump beam and the Stokes beam is achieved, and in SRS microscopy a phase-sensitive detector is employed to extract the heterodyning sample from the non-resonant background. In various embodiments, the stimulated Raman scattering may be excited by either one broadband laser pulse train or by two synchronized laser pulse trains with their difference frequency tuned to the vibrational frequency of a sample.

The detection system includes a filter that passes only the probe illumination, a mask, a lens and one or more photodetectors such as a photodiodes that generally surround the excitation path of the pump and probe beams. The photodetector is coupled to a demodulation unit (e.g., a phase sensitive detection device such as a lock-in amplifier), which is in turn coupled to a computer modulation source 81. A demodulation unit is also coupled to the modulation source 81 to ensure synchronization.

When the sample exhibits third order non-linear excitation vibrational resonance with a difference between the pump and Stokes fields, the sample will absorb heat due to the vibrational resonance. When this happens, the index of refraction of the focal area will change, and this will cause the probe beam to diverge. By employing the mask and the demodulation unit, the detection system may detect changes in the probe beam that are due to the changes in the index of refraction.

The local heating therefore, induces a local refractive index gradient, because the refractive index of most medium is temperature dependent. Such a local refractive index gradient forms effectively a thermal diverging lens, which can be further read out by a probe beam whose intensity is detected behind a mask such as an iris diaphragm. The intensity distribution of this probe beam at the objective focus could be specially shaped to sensitively sense the non-uniform local refractive index gradient. The objective may, therefore, be designed to control and shape the intensity distribution of the probe illumination so that a change in an index of refraction of a sample may be sensitively probed. Similarly, the mask in front of the far-field detector could also be specially designed to be conjugate with the intensity distribution of the probe beam at the focus.

To optimize the imaging sensitivity, phase sensitive detection may be utilized with modulation of the pump and/or Stokes at a high frequency (>10 kHz). The resulting probe illumination detected behind the mask will carry an intensity modulation at the same modulation frequency, which can be sensitively demodulated by a lock-in amplifier.

In accordance with further embodiments, a photo-thermal modulation transfer system may provide non-linear optical excitation using a two-photon laser source. The output of the two-photon source is modulated by a modulator at a modulation frequency. The second source provides probe illumination (for example, a continuous wave (CW) laser output or a high repetition rate laser output (e.g., 1 GHz) having a different frequency) that is combined with the modulated trains of laser pulses at a dichroic mirror 58. The combined modulated train of laser pulses and the probe laser output are then all provided to the objective lens that focuses the beams onto a focal area of a sample. The two photon excitation is provided therefore, by having two photons of relatively low energy excite a fluorophore through two-photon absorption of a molecule in the sample, resulting in the emission of a fluorescing photon.

Two-Color Two-Photon Absorption (TPA) and Transient Absorption

Modulation transfer microscopy and micro-spectroscopy may also be performed in accordance with various embodiments of the invention using two-color two-photon absorption techniques. Two-color two-photon absorption (TPA) techniques rely on the combined absorption of two photons by the sample and involve exciting the molecules into an excited electronic state. Chemical contrast is achieved by tuning the sum energy of the two photons into the energy of the electronic excited state. Femtosecond (fs) pulse-width lasers may be used to maximize the signal, but excitation with picosecond pulses is also possible for certain applications.

Stimulated Brillouin Scattering

Modulation transfer microscopy may also be performed using stimulated Brillouin Scattering microscopy, as well as cross-phase modulation in accordance with further embodiments of the invention.

Optical Assemblies

As shown in FIG. 5A, an optics assembly 152 of an embodiment of the invention receives the excitation illumination (including both the first and second trains of laser pulses) and focuses and directs the excitation illumination into a focal area 154 within a sample 156 using one or more objective lenses 150. Modulation transfer illumination that results from the non-linear optical interaction within the sample is directed in a forward direction (as discussed above with reference to FIG. 1C), and is back-scattered and reflected off material within the sample 156 that is outside of the focal area 154 as generally shown at 155. This scattered and reflected modulation transfer illumination is directed in many directions.

Applicants have discovered that, even though the objective lenses required for such excitation fields to produce the non-linear interaction with the sample are rather large and the focal distance is rather short, a substantial amount of the back-scattered and reflected modulation transfer illumination is scattered and reflected toward the area surrounding the objective lens 150 and/or surrounding the excitation path at the focal cone 158 of the distal objective lens of the lenses 150. A filter 160 (e.g., having an aperture in the middle) and a photo detector 162 (e.g., having an aperture in the middle) may therefore be positioned around the objective lens to provide for efficient filtering of illumination that is not of interest (e.g., the frequency of the modulated signal), while the photo detector receives the modulation transfer signal of interest as discussed above with reference to FIGS. 2, 3 and 4. An electrical modulation transfer signal as shown at 164 is then provided to an image processor. In various embodiments, the photo-detector may be formed of a variety of shapes, and may be provided as plurality of photo-detectors that generally surround the excitation axis Similarly, with regard to FIG. 5B, an optics assembly 172 of the an embodiment of the invention receives the excitation illumination and, using one or more objective lenses 170, focuses and directs the excitation illumination (including the first and second pulse trains) into a focal area 174 within a sample 176. Modulation transfer illumination is directed in a forward direction (as discussed above with reference to FIG. 1C), and is back-scattered and reflected off material within the sample 176 that is outside of the focal area 174 as generally shown at 175.

This back-scattered and reflected modulation transfer illumination is directed in many directions, and again applicants have discovered that a substantial amount of the scattered and reflected modulation transfer illumination is reflected toward the area surrounding the focal cone of the excitation path 178 from the distal objective lens. A filter 180 and a photo detector 182 (again both having apertures or being comprised of multiple elements) may therefore be positioned in front of the objective lens and around the excitation path to provide for efficient filtering of illumination that is not of interest, while the photo detector receives the modulation transfer signal of interest as discussed above with reference to FIGS. 2, 3 and 4. The optical assembly should also include a light buffer 186 for preventing any illumination from reaching the photo-detector 182 without first passing through the filter 180. An output electrical modulation transfer signal as shown at 184 is then provided to an image processor. The filter 180 may be placed in contact with the sample 176, and in certain embodiments, a protective coating may be applied to the sample or to the filter 180.

As shown in FIG. 5C, an optics assembly 192 in accordance with a further embodiment of the invention includes one or more objective lenses 190 that receive the excitation illumination and focus and direct the excitation illumination (including the first and second pulse trains) into a focal area 194 within a sample 196. Modulation transfer illumination is directed in a forward direction (as discussed above with reference to FIG. 1C), and (as shown at 195) is back-scattered and reflected off material within the sample 196 that is outside of the focal area 194. This reflected modulation transfer illumination is directed in many directions, and again applicants have discovered that a substantial amount of the scattered and reflected modulation transfer illumination is reflected toward the area surrounding the objective lens 190. A filter 200 and photo detector 202 may therefore be positioned around the objective lens to provide for efficient filtering of illumination that is not of interest, while the photo detector receives the modulation transfer signal of interest as discussed above with reference to FIGS. 2 and 3.

In the embodiment of FIG. 5C, the optics assembly 192 further includes waveguide material 193 (such as optical fibers or parabolic mirrors) that surrounding the objective lens(es) that direct the back-scattered and reflected modulation transfer signal toward the filter 200 and detector 202. In accordance with various embodiments, the filter 200 and detector 202 may be positioned at a remote location from the sample such that a waveguide extends away from the subject and directs the received illumination along a separate path from the path of the excitation optical fiber 102 (shown in FIG. 3). An electrical modulation transfer signal as shown at 206 is also provided to an image processor.

As shown in FIG. 5D, an optics assembly 212 in accordance with a further embodiment of the invention includes one or more objective lenses 210 that receive the excitation illumination and, using a gradient index (GRIN) lens focuses and directs the excitation illumination into a focal area 214 within a sample 216. Modulation transfer illumination is directed in a forward direction (as discussed above with reference to FIG. 1C), and (as shown at 215) is back-scattered and reflected off material within the sample 216 that is outside of the focal area 214. This modulation transfer illumination is directed in many directions, and again applicants have discovered that a substantial amount of the back-scattered and reflected modulation transfer illumination is reflected toward the area surrounding the objective lens 210.

A filter 220 and a photo detector 222 may therefore be positioned around the objective lens to provide for efficient filtering of illumination that is not of interest, while the photo detector receives the modulation transfer signal of interest as discussed above with reference to FIGS. 2, 3 and 4. An electrical modulation transfer signal is then provided as shown at 224. Similar to the embodiment of FIG. 5B, the filter 220 may be placed in contact with the sample 216, and a protective coating may be applied to the sample or the filter 220. The use of the GRIN lens may be employed to minimize the size (diameter) of the objective lens and to permit illumination to be collected close to the entrance pupil.

Figure 6:
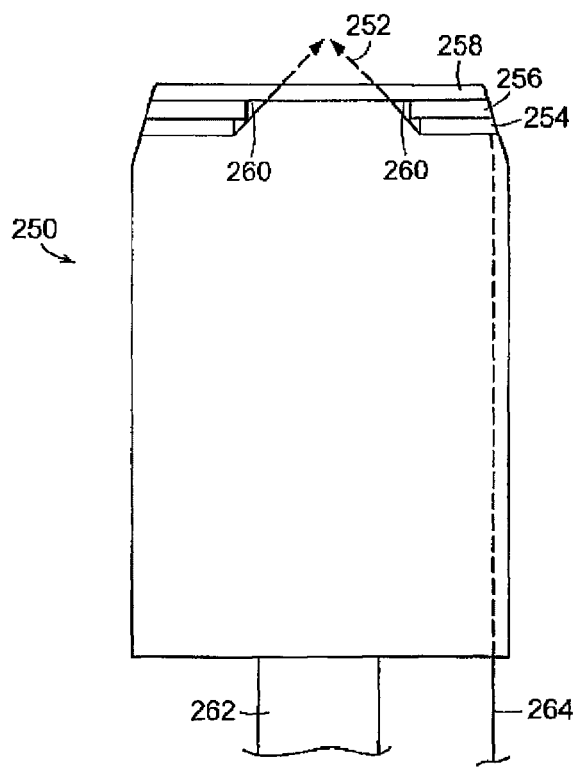
FIG. 6 shows an illustrative diagrammatic view of an optical assembly for use in a modulation transfer microscopy or micro-spectroscopy systems in accordance with a further embodiment of the present invention.

FIG. 6 shows a further embodiment of an optical assembly 250 in accordance with in embodiment of the invention that includes an object lens or set of lenses as discussed above with reference to FIGS. 5A-5D. The optical detector system of the optical assembly 250 includes an optical detector 254 and a filter 256 for removing illumination at the wavelength of the modulated excitation illumination field. The optical detector 254 and filter 256 generally surround the excitation illumination path 252. The assembly 250 also includes a glass cover 258 that may include an anti-reflective coating on the underside of the glass (nearer the objective lens), as well as a light baffle 260 surrounding the detector 254 and filter 256 to prevent illumination from reaching the detector 254 that has not passed from within the sample and through the filter 256 from reaching the detector 254. An optical fiber 262 provides the excitation fields (first and second trains of pulses) to the assembly, and an output electrical detector signal is provided as shown at 264.

Figure 7A:
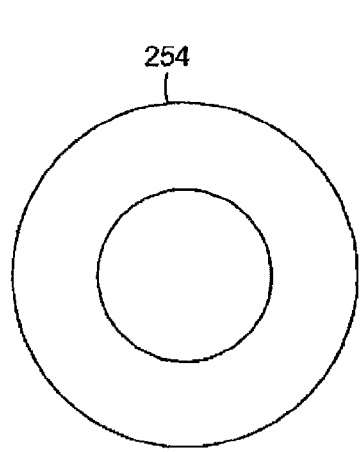
FIGS. 7A-7D show illustrative diagrammatic views of optical detector systems for use in a modulation transfer microscopy or micro-spectroscopy systems in accordance with different embodiments of the present invention.
Figure 7B:
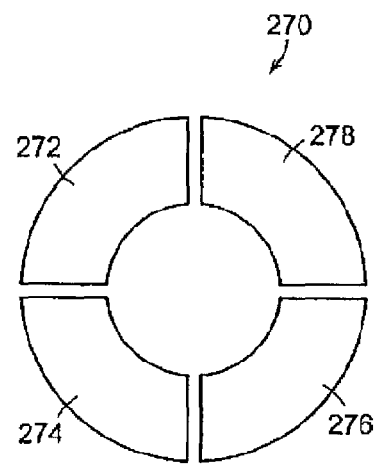
Figure 7C:
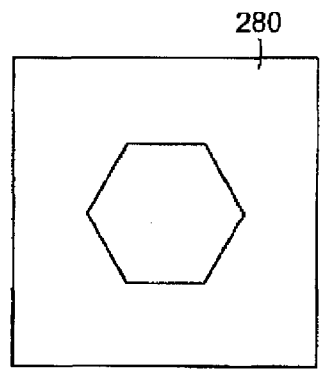
Figure 7D:
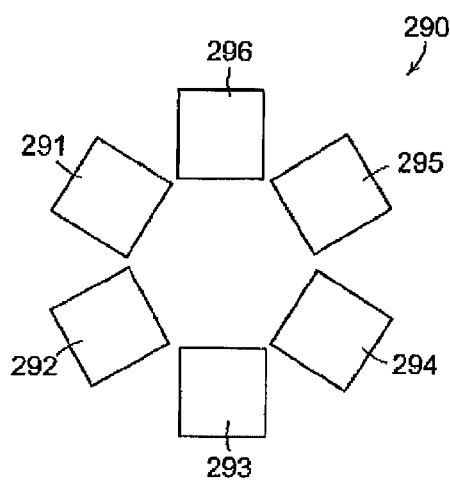

The detector assembly may include a single annular shaped photo-diode 254 as shown in FIG. 7A. In further embodiments, the detector assembly 270 may include a plurality of photo-diodes 272, 274, 276 and 278, as shown in FIG. 7B, that collectively surround the excitation illumination path.252. In further embodiments as shown in FIG. 7C, the photo-detector 280 may be formed of any shape (e.g., square) and include an aperture of any shape, and as shown in FIG. 7D, the detector assembly 290 may include a plurality of photo-diodes 291-296 that also may be formed of any shape. The modulation transfer signal of interest may, therefore, be detected with an annular-shaped photodiode or a set of photodiodes that are arranged to generally surround a portion of the excitation path. In the shot-noise limit (relative signal noise ~1/√(number of photons detected)) the imaging speed may be increased by increasing the number of photons detected maintaining the same relative noise. It is therefore important that the photodiode allows the detection of high laser intensities (typically ~200 mW). The use of a large-area photodiode allows small variation of the detected signal even if the beams are slightly moving on the photodiode (see non-descanned detection below). The response-time however, has to be short enough to allow high-frequency modulation. Silicon or Germanium diodes allow covering the necessary wavelength regime in the near IR. A commercially available system such as a Thorlabs FDS1010 system may be used.

A high optical density blocking filter is needed in front of the light detector to suppress the signal that is not of interest (e.g., the modulated pump beam for Raman Gain microscopy or Stokes beam for Raman Loss microscopy), while passing the wanted signal (e.g., the Stokes beam or pump beam). A system such as a Chroma Tech 890/220 band-bass filter (for Raman Loss microcopy) may be used to block 1064 nm Stokes beam while pass the pump beam.

The challenge on the detection side is to extract the signal from a huge background as the technique measures a small intensity increase (Raman Gain)/decrease (Raman Loss) off the strong laser intensities:

$$\text{Intensity after the sample} \approx |E_0 \pm \Delta E|^2 = E_0^2 \pm \Delta E \cdot E_0 + \Delta E^2$$

where $E_0$ is the electric field of the excitation beam (Stokes beam for Raman Gain and pump beam for Raman Loss) and $\Delta E$ is the radiation at the same frequency due to the nonlinear third-order induced polarization. Because of the coherent increase/decrease the resulting laser intensity after the sample (proportional to the absolute value of the electric field squared) consists of the original laser intensity, the coherent mixing term and the quadratic term of the field change. For typical samples and laser intensities used, the mixing term is more than 5 orders of magnitude lower and the quadratic term is more than 10 orders of magnitude lower than the intensity of the incoming laser beam. Thus the quadratic term is negligible and the challenge of the detection is to extract the relatively small heterodyning term from the huge laser background. If this suppression is incomplete, laser-noise scaling with the background overwhelms the relatively small signal.

High-frequency modulation with phase-sensitive detection is employed to extract the heterodyning signal from the background. Some type of modulation is used to modulate the intensity of the signal (e.g., amplitude modulation, time-delay modulation or frequency modulation) keeping the background constant. In a frequency perspective the signal occurs at the modulation frequency $\omega_{mod}$ whilst the background is DC. By electronically filtering out all contributions but the signal at $\omega_{mod}$ it is possible to reject the background. The bandwidth of this filter is $\sim 1/T_{int}$, where $T_{int}$ is the integration time constant (equals the pixel dwell time). Considering phase with respect to the modulation as a second characteristic of the signal compared to the background and its noise, a more complete suppression is possible. A lock-in amplifier may be used to achieve this.

The excitation lasers are not constant in intensity but have intensity-noise which is spectrally broad. This introduces components of the laser (not the signal) at $\omega_{mod}$ that are purely due to noise and would limit the sensitivity of the technique if not minimized. The intensity of the laser noise typically depends inversely on the frequency (1/f noise). Thus by choosing $\omega_{mod}$ high enough the contribution from the laser-noise within the detection-bandwidth of the lock-in amplifier becomes small. For the OPO system described above a modulation >1 MHz will typically suppress the laser-noise completely, or makes the laser noise negligible compared to the signal size.

By scanning the focal spot through the sample and measuring the signal for every pixel it is possible to build up a 3-dimensional image of the distribution of the molecular species. This scanning may be done either by beam-scanning (e.g., scan the focal spot through the fixed sample by changing the angles of the beams at the back-aperture of the objective with respect to normal incidence), stage-scanning (e.g., moving the sample with respect to the fixed focal spot) or any combination these. With beam-scanning, scan-rates as high as 7000 lines/s can be achieved, it is mechanically more stable and does not perturb the sample as is remains unmoved. Most commercially available confocal microscopes use a combination of beam-scanning in the x y-plane and stage-scanning in z. An Olympus FV-300 or FV-1000 system, Leica SP5, or Zeiss LSM 510 or LSM 710 system may be used for this.

Optical Assemblies with Scanning Assemblies

Figure 8A:
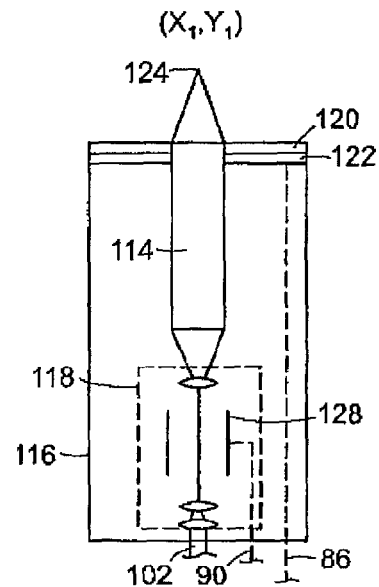
FIGS. 8A and 8B show illustrative diagrammatic views of a scanning optical detector system for use in a modulation transfer microscopy or micro-spectroscopy systems in accordance with different embodiments of the present invention employing an electro-optic switch.
Figure 8B:
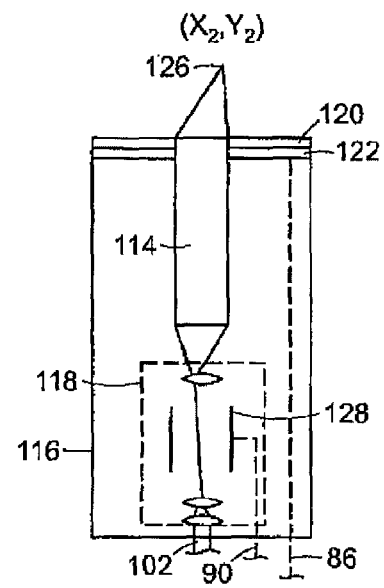

As shown in FIGS. 8A and 8B, an optics assembly 116 in accordance with a further embodiment of the invention includes a scanning assembly 118 that receives the excitation illumination, and a gradient index (GRIN) lens 114 that focuses and directs the excitation illumination into a focal area 124 within a sample. Modulation transfer illumination is directed in a forward direction (as discussed above with reference to FIG. 1C), and is back-scattered and reflected off material within the sample that is outside of the focal area as discussed above with reference to FIGS. 5A-5D. This modulation transfer illumination is directed in many directions, and again applicants have discovered that a substantial amount of the back-scattered and reflected modulation transfer illumination is reflected toward the area surrounding the objective lens 114.

A filter 120 and a photo detector 122 are positioned around the objective lens 114 to provide for efficient filtering of illumination that is not of interest, while the photo detector receives the modulation transfer signal of interest as discussed above with reference to FIGS. 2, 3 and 4. An electrical modulation transfer signal is then provided as shown at 86. The filter 120 may be placed in contact with the sample, and/or a protective coating may be applied to the sample or the filter. The use of the GRIN lens may be employed to minimize the size (diameter) of the objective lens and to permit illumination to be collected close to the entrance pupil.

As also shown in FIGS. 8A and 8B, the optical assembly 116 also includes a scanning assembly 118 that receives the excitation illumination from the optical fiber 102. Using one or more electro-optic scanning elements (e.g., one positioned as shown at 128 to provide x direction scanning and another positioned orthogonally disposed to the one shown to provide y direction scanning), the scanning assembly moves the focal area from that shown at $(x1, y_1)$ as shown at 124 in FIG. 8A to a different focal area $(x_2, y_2)$ as shown at 126 in FIG. 8B. In particular, the one or more electro-optic scanning elements 128 move the excitation illumination responsive to a position control signal 90 to a different position prior to the objective lens 114 such that the resulting focal area may be moved in the x and y directions. The electro-optic scanning elements may be as disclosed, for example, in U.S. Pat. No. 5,124,835, the disclosure of which is hereby incorporated in its entirely by reference.

Figure 9A:
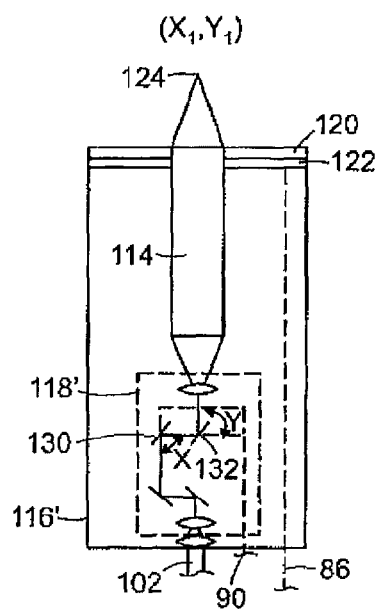
Figure 9B:
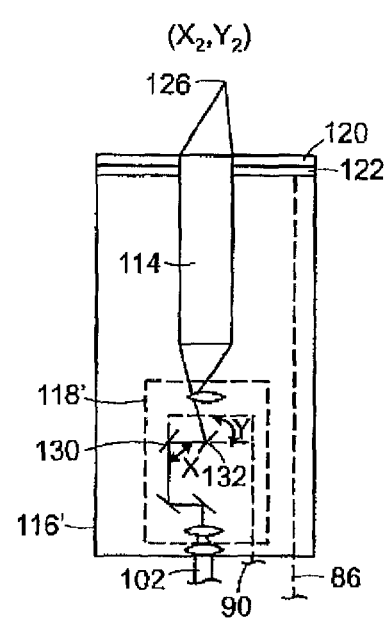

As shown in FIGS. 9A and 9B, an optics assembly 116' in accordance with a further embodiment of the invention includes a scanning assembly 118' that receives the excitation illumination, and the gradient index (GRIN) lens 114 that focuses and directs the excitation illumination into the focal area 124 within a sample. Modulation transfer illumination is directed in a forward direction (as discussed above with reference to FIG. 1C), and is back-scattered and reflected off material within the sample that is outside of the focal area as discussed above with reference to FIGS. 5A-5D. This modulation transfer illumination is directed in many directions, and again applicants have discovered that a substantial amount of the back-scattered and reflected modulation transfer illumination is reflected toward the area surrounding the objective lens 114.

Again, the filter 120 and photo detector 122 are positioned around the objective lens 114 to provide for efficient filtering of illumination that is not of interest, while the photo detector receives the modulation transfer signal of interest as discussed above with reference to FIGS. 2, 3 and 4. The electrical modulation transfer signal is then provided as shown at 86. The filter 120 may be placed in contact with the sample, and/or a protective coating may be applied to the sample or the filter. The use of the GRIN lens may be employed to minimize the size (diameter) of the objective lens and to permit illumination to be collected close to the entrance pupil.

The optical assembly 116' also includes a scanning assembly 118' that receives the excitation illumination from the optical fiber 102. Using a selectively positionable x mirror 130 and a selectively positionable y mirror 132, the scanning assembly moves the focal area from that shown at $(x_1, y_1)$ as shown at 124 in FIG. 9A to a different focal area $(x_2, y_2)$ as shown at 126 in FIG. 9B. In particular, the positionable x and y mirrors move the excitation illumination responsive to a position control signal 90 to a different position prior to the objective lens 114 such that the resulting focal area may be moved in the x and y directions. The positionable mirrors 130, 132 may be small galvanometer scanner motors, or may be micro-electro-mechanical scanner (MEMS) elements.

As shown in FIGS. 10A and 10B, an optics assembly 116" in accordance with a further embodiment of the invention includes a scanning assembly 118" that receives the excitation illumination, and the gradient index (GRIN) lens 114 that focuses and directs the excitation illumination into the focal area 124 within the sample. Modulation transfer illumination is directed in a forward direction (as discussed above with reference to FIG. 1C), and is back-scattered and reflected off material within the sample that is outside of the focal area as discussed above with reference to FIGS. 5A-5D. This modulation transfer illumination is directed in many directions, and again applicants have discovered that a substantial amount of the back-scattered and reflected modulation transfer illumination is reflected toward the area surrounding the objective lens 114.

Again, the filter 120 and photo detector 122 are positioned around the objective lens 114 to provide for efficient filtering of illumination that is not of interest, while the photo detector receives the modulation transfer signal of interest as discussed above with reference to FIGS. 2, 3 and 4. The electrical modulation transfer signal is then provided as shown at 86. The filter 120 may be placed in contact with the sample, and/or a protective coating may be applied to the sample or the filter. The use of the GRIN lens may be employed to minimize the size (diameter) of the objective lens and to permit illumination to be collected close to the entrance pupil.

The optical assembly 116" also includes a scanning assembly 118" that receives the excitation illumination from the optical fiber 102. Using a single micro-electro-mechanical (MEMS) scanner 134 to position the excitation illumination in x and y directions, the scanning assembly moves the focal area from that shown at $(x_1, y_1)$ as shown at 124 in FIG. 10A to a different focal area $(x_2, y_2)$ as shown at 126 in FIG. 10B. In particular, the x, y MEMS scanner scans the excitation illumination in both x and y directions independently by resonating very small reflectors in both x and y directions. The reflectors may be formed of single crystalline silicon on a silicon-on-insulator substrate in banks of combs that may be resonated in both x and y directions as disclosed, for example, in *Fast-Scanning Two-Photon Fluorescence Imaging Based on a Microelectromechanical Systems Two-Dimensional Scanning Mirror*, by W. Piyawattanametha et al., Optics Letters, 31 (13): 2018, Jul. 1, 2006, the disclosure of which is hereby incorporated in its entirety by reference.

As shown in FIGS. 11A and 11B, an optics assembly 116' in accordance with a further embodiment of the invention includes a scanning assembly 118' that receives the excitation illumination, and a lens 114 (e.g., a gradient index (GRIN) lens) that focuses and directs the excitation illumination into the focal area 124 within the sample. Modulation transfer illumination is directed in a forward direction (as discussed above with reference to FIG. 1C), and is back-scattered and reflected off material within the sample that is outside of the focal area as discussed above with reference to FIGS. 5A-5D. This modulation transfer illumination is directed in many directions, and again applicants have discovered that a substantial amount of the back-scattered and reflected modulation transfer illumination is reflected toward the area surrounding the objective lens 114.

Again, the filter 120 and photo detector 122 are positioned around the objective lens 114 to provide for efficient filtering of illumination that is not of interest, while the photo detector receives the modulation transfer signal of interest as discussed above with reference to FIGS. 2, 3 and 4. The electrical modulation transfer signal is then provided as shown at 86. The filter 120 may be placed in contact with the sample, and/or a protective coating may be applied to the sample or the filter. The use of the GRIN lens may be employed to minimize the size (diameter) of the objective lens and to permit illumination to be collected close to the entrance pupil.

The optical assembly 116''' also includes a scanning assembly 118' that receives the excitation illumination from the optical fiber 102. Using a quartered piezo tube actuator 136, the fiber 102 is driven (resonated) near the scanning fiber's fundamental mode of lateral resonance such that a tip portion as shown at 140 resonantly moves in x and y directions. The piezo tube actuator 136 may be formed as a quartered tube that provides a pair of opposing x direction actuators and a pair of opposing y direction actuators. The quartered piezo tube actuator 136 is used to move the excitation illumination in x and y directions, to provide that the scanning assembly moves the focal area from that shown at $(x_1, y_1)$ as shown at 124 in FIG. 11A to a different focal area $(x_2, y_2)$ as shown at 126 in FIG. 11B. In particular, the quartered piezo tube actuator 136 may be as disclosed, for example, in Scanning Fiber Endoscopy with Highly Flexible, 1 mm, Catheterscopes for Wide-Field, Full Color Imaging, by C. Lee et al., Journal of Bio-Photonics, 3, No. 5-6, pages 385-407 (2010), the disclosure of which is hereby incorporated in its entirety by reference.

Figure 12A:
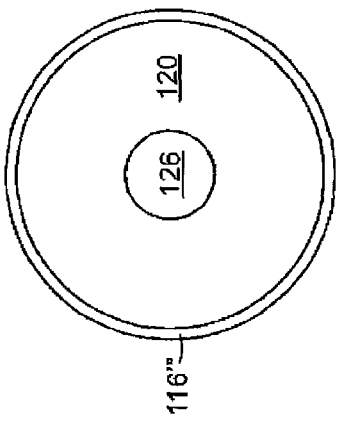
FIGS. 12A and 12B show illustrative diagrammatic end views of scanning optical detector systems in accordance with various embodiments of the invention.
Figure 12B:
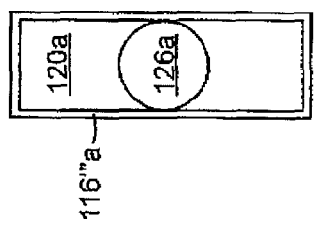

As shown in FIG. 12A, the distal end of the optical assembly (e.g., 116''' of FIGS. 11A and 11B) may include a disc-shaped filter (e.g., 120) and a disc-shaped photo detector (e.g., 122), each of which has an opening in their center through which the excitation fields (e.g., 126) pass upon exciting the optical assembly. For convenience, such an assembly may be packaged within an optical assembly having approximately the same diameter (e.g., under 20 mm, and preferably about 5 mm) as the disc-shaped filter and photo detector. In accordance with further embodiments, the optical assembly may not be disc shaped in its end view, but may instead be rectangular (as shown at 116'''a in FIG. 12B), having rectangular shaped filter (as shown at 120a) and a rectangular shaped photo detector under filter, each of which has an opening in the center through which the excitation fields 126a pass. A benefit of the embodiment of FIG. 12B is that the size (area) of the end of the optical assembly may be made smaller, although at a cost of not collecting some of the signal information from the sample since the detector area is smaller. In each of the embodiments of FIGS. 12A and 12B, a further support structure may be provided on the proximal surface (backside) of the photo detectors to provide additional structural support.

Figure 13A:
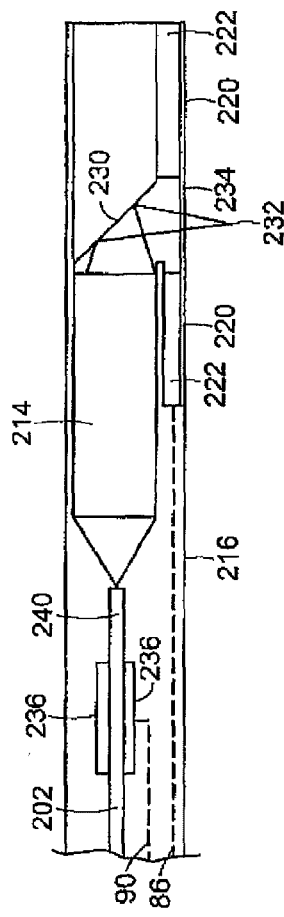
FIGS. 13A and 13B show illustrative diagrammatic side and bottom views of a scanning system optical detector system in accordance with another embodiment of the invention.
Figure 13B:
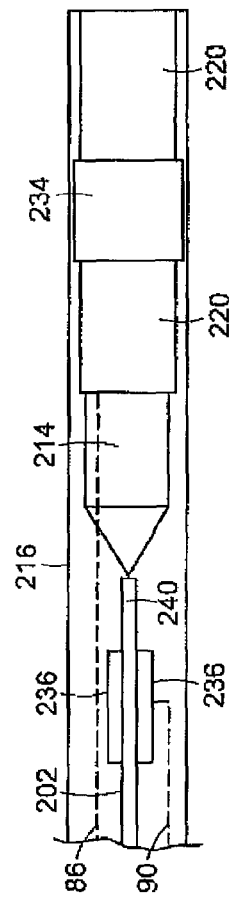

FIGS. 13A and 13B show an embodiment of an optical assembly in accordance with a further embodiment of the invention wherein the size (area) of the distal end of the detector is made even smaller by folding the excitation fields such that imaging is achieved on a side of the optical assembly rather than at the distal end. In particular, as shown in FIG. 13A, the optical assembly 216 includes a fiber 202 that receives excitation illumination from a source system as discussed above with reference to FIG. 4. As discussed above with reference to FIGS. 11A and 11B, using a quartered piezo tube actuator 236, the fiber 202 is driven (resonated) near the scanning fiber's fundamental mode of lateral resonance such that a tip portion as shown at 240 resonantly moves in x and y directions. The piezo tube actuator 236 may be formed as a quartered tube that provides a pair of opposing x direction actuators and a pair of opposing y direction actuators. The quartered piezo tube actuator 236 is used to move the excitation illumination in x and y directions, to provide that the scanning assembly moves the focal area as discussed above to a different focal area. In particular, the quartered piezo tube actuator 236 may be as disclosed above with reference to FIGS. 11A and 11B.

One or more control signals 90 may be provided to the piezo tube actuator 236 to control the movement of the tip portion 240. A lens 214 (such as for example a GRIN lens) receives illumination from the scanning tip portion 240 and directs the illumination via a mirror 230 through a glass cover 234 to a focal area 232 on a side of the optical assembly 216. Illumination from the sample is then reflected back toward the optical assembly 216, is filtered by filters 220, and is received by photo detectors 222. An electrical modulation transfer signal (as shown at 86) is provided from the photo detectors 222 to a pixel image processor 84 as discussed above with reference to FIG. 4. The optical assembly 216 of FIGS. 13A and 13B permits the size of the distal portion of the assembly to be very small, e.g., having end area dimensions of about 2 mm by 2 mm or less. Detection of the modulation transfer signal of interest, however, must be achieved using only the detector areas 222 that are behind the filters 220 and are proximate the path of the excitation fields as shown in FIG. 13B.

Figure 14A:
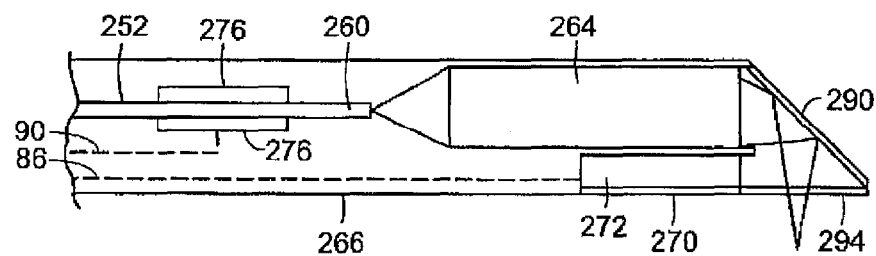
FIGS. 14A and 14B show illustrative diagrammatic side and bottom views of a scanning system optical detector system in accordance with further embodiment of the invention.
Figure 14B:
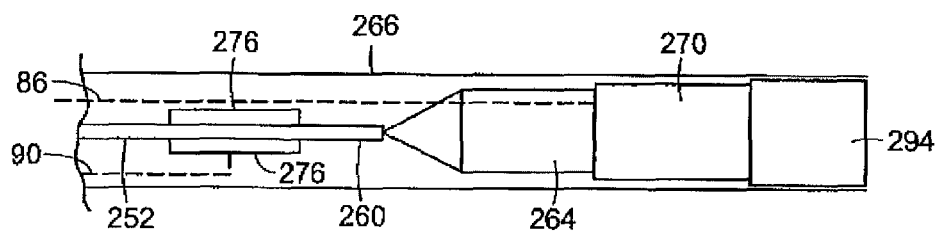

In accordance with further embodiments where the modulation transfer signal of interest may be particularly strong, only the proximal detector area may be used. For example, FIGS. 14A and 14B show and optical assembly 266 includes a fiber 252 that receives excitation illumination from a source system as discussed above with reference to FIG. 4. As discussed above with reference to FIGS. 11A and 11B, using a quartered piezo tube actuator 276, the fiber 252 is driven (resonated) near the scanning fiber's fundamental mode of lateral resonance such that a tip portion as shown at 280 resonantly moves in x and y directions. The piezo tube actuator 276 may be formed as a quartered tube that provides a pair of opposing x direction actuators and a pair of opposing y direction actuators. The quartered piezo tube actuator 276 is used to move the excitation illumination in x and y directions, to provide that the scanning assembly moves the focal area as discussed above to a different focal area. In particular, the quartered piezo tube actuator 276 may be as disclosed above with reference to FIGS. 11A and 11B.

One or more control signals 90 may be provided to the piezo tube actuator 276 to control the movement of the tip portion 280. A lens 264 (such as for example a GRIN lens)

receives illumination from the scanning tip portion 280 and directs the illumination via a mirror 290 through a glass cover 294 to a focal area 292 on a side of the optical assembly 266. Illumination from the sample is then reflected back toward the optical assembly 266, is filtered by a filter 270, and is received by a photo detector 272. An electrical modulation transfer signal (as shown at 86) is provided from the photo detectors 272 to a pixel image processor 84 as discussed above with reference to FIG. 4. The optical assembly 266 of FIGS. 14A and 14B also permits the size of the distal portion of the assembly to be very small, e.g., having end area dimensions of about 2 mm by 2 mm or less as discussed above with reference to FIGS. 13A and 13B, but provides an angled distal end that may be more convenient for certain applications. Detection of the modulation transfer signal of interest, however, must further be achieved using only the detector area 272 that is behind the filter 270 and is proximate the path of the excitation fields as shown in FIG. 14B.

In the above systems of FIGS. 8A-13B, the scanning assemblies may be driven by a position signal (e.g., for independent x and y scanners). In other embodiments, however, the scanning assemblies may be resonated (e.g., the MEMS element or the piezo tube actuator may be operated) at a fixed resonance, and a timing signal may be employed to ensure that the lasers fire (or laser fires) when the excitation field is in a desired position. The scanning paths may be formed of a variety of patterns that most suitably employ the resonant motion of the scanner. For example, if the piezo tube actuator is resonated in x and y directions respectively by excitation signals having varying amplitudes that follow sine and cosine signals, then the resulting movement of the excitation illumination prior to the objective lens (as well as the path of movement of the focal area) will follow a circular pattern that begins at the center and spirals outward with increasing radius as disclosed in *Scanning Fiber Endoscopy with Highly Flexible, 1 mm, Catheterscopes for Wide-Field, Full Color Imaging*, by C. Lee et al., Journal of Bio-Photonics, 3, No. 5-6, pages 385-407 (2010).

Figure 15:
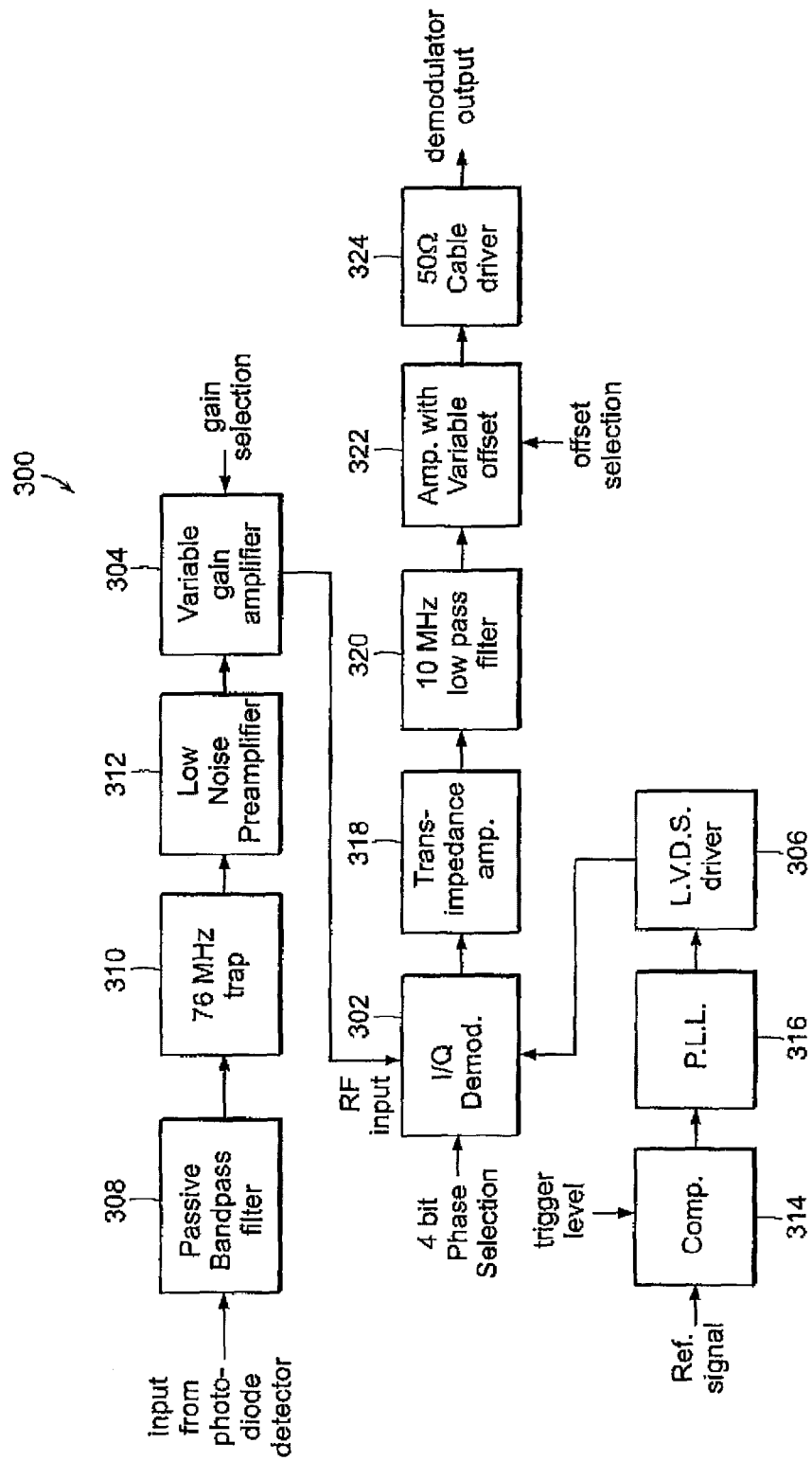
FIG. 15 shows a diagrammatic functional view of a lock-in detector used in a system in accordance with an embodiment of the invention.

FIG. 15A shows that reducing the size of the excitation objective lens allows for more efficient collection. In particular, collection using a cortex emission profile lens is shown at 400, using an Olympus 0.5 NA Needle objective is shown at 402, and using an Olympus 0.7 NA Needle objective is shown at 404. Compared with complete detection of the back-scattered light from cortex tissue (38%) as shown at 400, an example excitation objective with 3.5 mm outer diameter allows collection with a surrounding detector with 23% efficiency (shown at 404), and an even smaller excitation objective with 1.8 mm outer diameter with 33% efficiency (shown at 402).

FIG. 15B shows cumulative irradiance as a function of the radius of the aperture. The cumulative irradiance as a function of the radius when the detector is set back from the aperture by 5 mm is shown at 410, by 3 mm is shown at 412, by 2 mm is shown at 414, by 1 mm is shown at 316 and by 0 mm us shown at 418. The cumulative irradiance using a cortex emission profile and a 0.7 NA (set 3.5 mm from the aperture) is shown at 420. Optical filters in from the detector should be chosen to be thin. Compared to a filter coated directly onto the detector (i.e., a detector 0 mm from the front aperture), collection efficiency decreases from 24% to 18% if the filter has a thickness of 5 mm.

FIG. 15C shows the angular dependence of cumulative illumination as a function of radius for a variety of angles. For example FIG. 12C shows the response at 430 if the angle is 90 degrees (directly above the detector), shows the response at 432, 434, 436, 438, 440, 442, 444 and 446 if the angle is 80 degrees, 70 degrees, 60 degrees, 50 degrees, 40 degrees, 30 degrees, 20 degrees and 10 degrees respectively. As diffuse light is detected, all spatial angles of back-scattered light need to be detected with high efficiency. Anti-reflective coatings and high numerical aperture (NA) collection optics may also be used. The optical filter may also be designed to block illumination from all of these angles. Absorbing filters may also be helpful in certain applications.

FIG. 15D shows the cumulative irradiance dependence on radius using a variety of numerical aperture sizes. The cumulative irradiance for a numerical aperture size of 1.1 NA (cortex emission profile) is shown at 450, for a numerical aperture size of 0.5 NA (cortex emission profile) is shown at 452, and for a numerical aperture size of 0.7 NA (cortex emission profile) is shown at 454. As may be seen from FIG. 15D, the NA of the excitation objective is not particularly important for efficient collection using collection devices of the present invention.

Example

An experimental example of a system as shown in FIG. 4 having an optical assembly of FIGS. 11A and 11B was built as follows. Synchronized, mode-locked laser pulse trains were provided by an optical parametric oscillator that was synchronously pumped by a frequency doubled Nd:YVO4 laser (532 nm, 7 ps, 76 MHz repetition rate). The Stokes beam (1064 nm) was modulated by a Pockel cell electro-optic modulator at 20.8 MHz to provide polarization modulation that was then transformed to amplitude modulation by a polarization analyzer, and was spatially overlapped with the pump beam (523 nm) using a dichroic mirror. The combined beams were aligned into a laser scanning microscope and were focused by the objective assembly onto a common focal spot. The common focal spot was scanned through the specimen by a galvanometer mirror and a resonant mirror. The detected intensity of the backscattered pump beam was demodulated with a lab-build all-analog lock-in amplifier to provide the SRS signal to the computer. The optical assembly included a detector system, and the sample is excited by focusing the illumination through a small hole in the center of the large-area epi-photo-diode detector. Scattering re-directs a significant portion (e.g., 20%) of the forward-traveling light to illuminate the detector active area. The modulated Stokes beam is blocked by an optical filter, and the transmitted pump beam is detected.

Figure 16A:
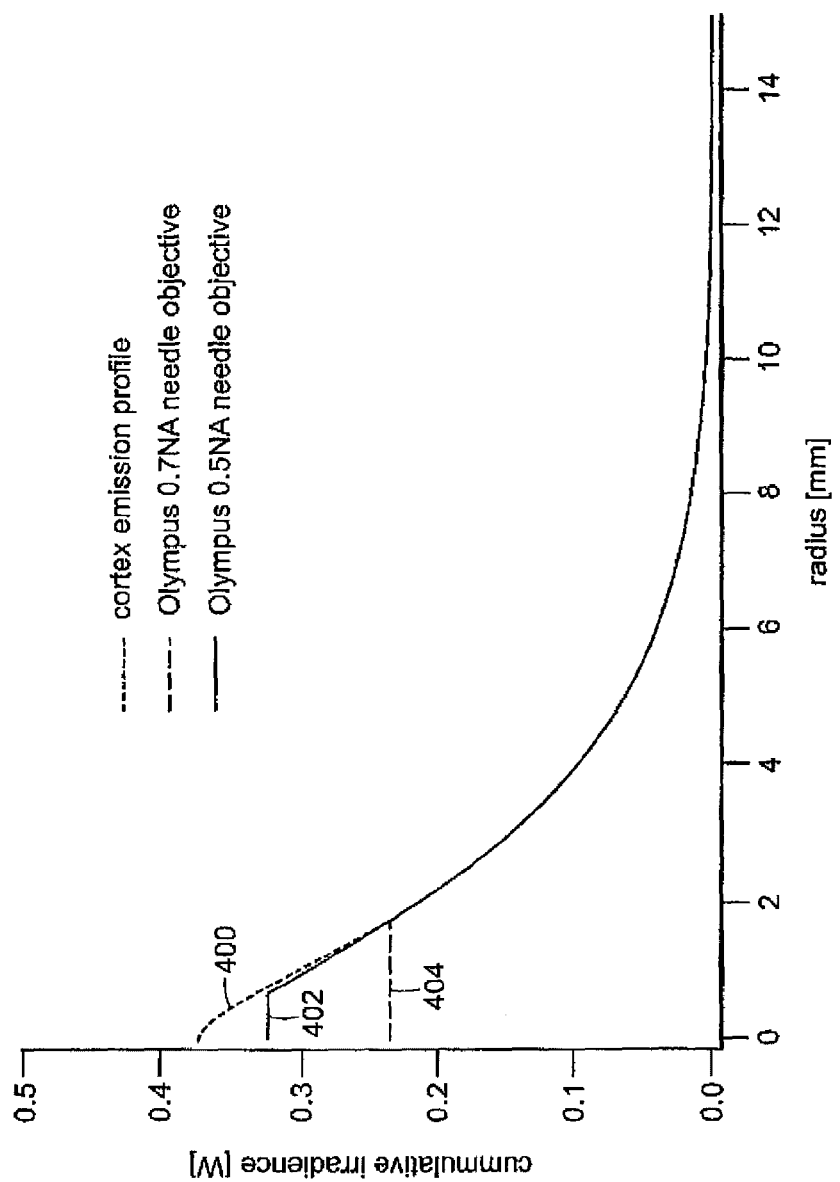

With reference to FIG. 16, the all-analog lock-in amplifier 300 included an I/Q demodulator 302 that received a 4 bit phase selection input, an input from a variable gain amplifier 304 in an RF signal path, and an input from a low-voltage differential signaling (LVDS) driver 306 from a LO signal path. The variable gain amplifier receives input from the photo-diode detector via a passive bandpass filter 308, a 76 MHz trap 310 and a low noise amplifier 312 as shown. A comparator 314 receives a reference signal and a trigger level signal, and provides an output to a phase locked loop 316, which in turn provides an output to the LVDS driver 306. The output of the I/Q demodulator 302 is provided to a transimpedance amplifier 318, then to a 10 MHz low pass filter 320, then to an amplifier (e.g., 10×) having a variable offset 322 (that is adjustable using an offset selection input), and is output as the demodulated output by a 50 Ohm cable driver 324. The entire lock-in amplifier system was placed within a shielded enclosure to minimize coherent pickup from the environment.

The optical detector system included a silicon PiN photo-diode having a central hole of about 2.1 mm diameter and a filter formed by sputter coating a fused silica surface, again with a 2.1 mm diameter central hole therein. Standoff edging tapes were also provided at the edges of the photodetector surface to provide an air buffer layer between the photodetector and the filter. The interior of the hole in the filter and photodiode were coated with an opaque material (carbon black paint) to avoid leakage through the hole.

In Vivo Imaging

For video rate imaging, the pixel dwell time may be about 110 ns and the modulation frequency must be high enough to permit at least one modulation cycle per pixel. To achieve high speed imaging, for example, the intensity of the Stokes beam was modulated at 20.8 MHz and the above-discussed lab-built all-analog lock-in amplifier was used having a response time of about 100 ns. The modulation transfer in an SRS system resulting intensity loss of the pump beam was determined.

Figure 17A:
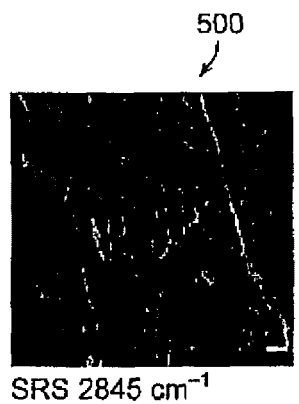
FIGS. 17A-17E show illustrative in vivo micro-photographic skin images of an animal obtained at video rate using a modulation transfer (SRS) imaging system in accordance with an embodiment of the invention.
Figure 17B:
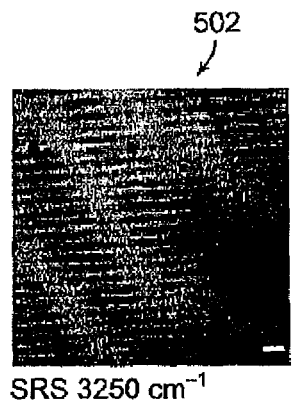
Figure 17C:
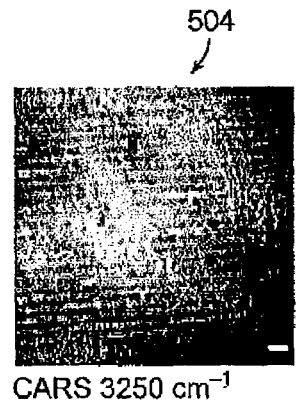
Figure 17D:
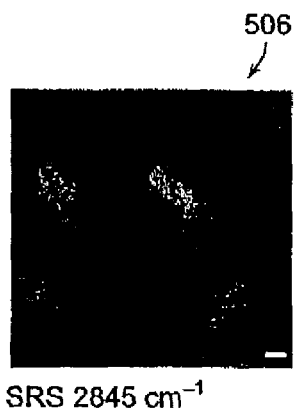
Figure 17E:
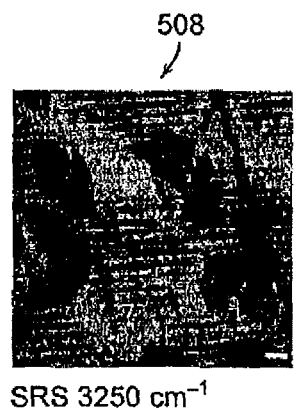
Figure 18A:
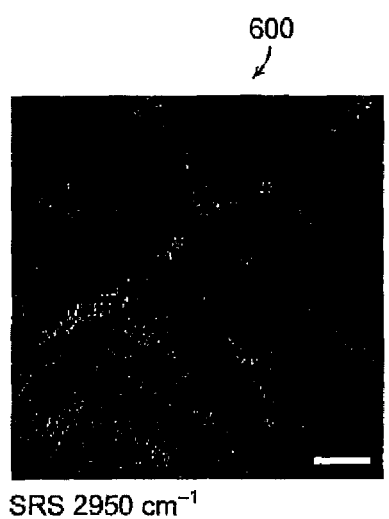
FIGS. 18A-18D show illustrative in vivo micro-photographic images of human skin obtained at video rate using a modulation transfer (SRS) imaging system in accordance with an embodiment of the invention.
Figure 18B:
Figure 18C:
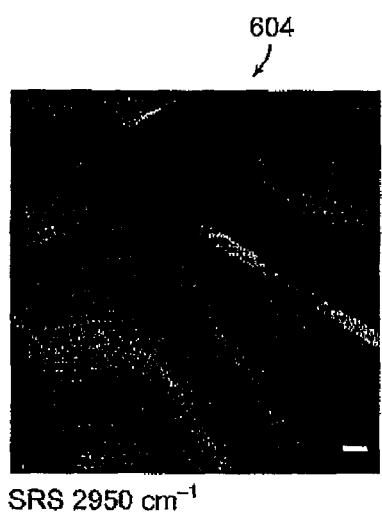
Figure 18D:

Using the above system, skin images in mice were obtained in vivo, and showed $CH_2$ stretching vibrations (primarily lipids), OH stretching vibrations (primarily water), and $CH_3$ stretching (primarily protein) vibrations. FIGS. 17A-17E show images obtained at video rate in accordance with an embodiment of the invention. FIG. 17A shows at 500 an SRS image of lipids of the statum corneum, showing intercellular spaces between hexagonal corneocytes. FIG. 17B shows at 502 an SRS image (3250 $cm^{-1}$) of the same region as that of FIG. 17A showing a homogenous distribution of water. Water may only be measured in vivo because the skin hydration changes in excised tissue. Imaging water is of particular interest in studying the transport properties of water soluble drugs and their effect on the hydration of the skin barrier. FIG. 17C shows at 504 a CARS water image that was acquired simultaneously with the image of FIG. 17B, showing artifacts from the non-resonant background of lipids (which are not present in FIG. 17B). FIG. 17D shows at 506 an image of lipid and FIG. 17E shows at 508 an image of water of a viable epidermis using an SRS system in accordance with an embodiment, showing sebaceous glands with positive and negative contrast respectively.

FIGS. 18A-18D show skin images in a living human subject of the stratum corneum and viable epidermis tuned into $CH_3$ stretching vibrations of proteins (2950 $cm^1$) showing nuclei of variable sizes (as shown at 600 in FIGS. 19A and 602 in FIG. 19B), as well as hair (as shown at 604 in FIGS. 19C and 606 in FIG. 19D). The image acquisition time was 150 ms for FIGS. 18A and 18B, and was 37 ms for FIGS. 18C and 18D, each with 512×512 pixel sampling and a scale of 50 μm.

Powerful label-free in vivo video rate imaging may be achieved in accordance with various embodiments of the invention to yield insight into the transport of small molecules into a subject and in providing in vivo imaging for medical diagnostics.

Those skilled in the art will appreciate that numerous modifications and variations may be made to the above disclosed embodiments without departing from the spirit and scope of the claims.

What is claimed is:

1. A microscopy or micro-spectroscopy system comprising:
    a first light source for providing a first illumination field at a first optical frequency $\omega_1$;
    a second light source for providing a second illumination field at a second optical frequency $\omega_2$;
    a modulator for modulating a property of the second illumination field at a modulation frequency f of at least 100 kHz to provide a modulated second illumination field;
    an optical assembly including focusing optics and an optical detector system,
        said focusing optics for directing and focusing the first illumination field and the modulated second illumination field through an objective lens toward the common focal volume along an excitation path; and
        said optical detector system including at least one optical detector for detecting a detected first field intensity of the first illumination field that is back-scattered within a sample, wherein said optical detector provides an electrical signal representative of the detected first field intensity, and said optical detector is located proximate a portion of the excitation path; and
    a processor for detecting a modulation at the frequency f of the electrical signal due to non-linear optical interaction within the common focal volume.

2. The system as claimed in claim 1, wherein said optical detector system substantially surrounds a portion of the excitation path.

3. The system as claimed in claim 1, wherein said processor provides an output signal that is representative of one of a gain or loss of illumination at the first optical frequency $\omega_1$ due to the non-linear optical interaction within the common focal volume.

4. The system as claimed in claim 1, wherein illumination at a difference frequency between $\omega_1$ and $\omega_2$ is resonant with a molecular vibrational frequency of the sample in the focal volume.

5. The system as claimed in claim 1, wherein one of said first and second illumination fields is a broadband illumination field.

6. The system as claimed in claim 1, wherein one of the first illumination field or the second illumination field is resonant with an electronic absorption of the sample.

7. The system as claimed in claim 6, wherein the second illumination field excites molecules in the sample into an excited state.

8. The system as claimed in claim 6, wherein the second illumination field removes molecules from a ground state by promoting them to an excited state.

9. The system as claimed in claim 1, wherein a sum frequency of the first illumination field and the second illumination field is resonant with a two-photon electronic absorption of the sample.

10. The system as claimed in claim 1, wherein said optical detector system includes a photo-diode having a central aperture through which the excitation path extends.

11. The system as claimed in claim 1, wherein said optical detector system includes a plurality of photo-diodes that collectively surround the excitation path.

12. The system as claimed in claim 1, wherein said processor provides a pixel signal that is representative of the modulation at the frequency f of the electrical signal due to non-linear optical interaction within the common focal volume as a pixel for an image for an imaging system.

13. The system as claimed in claim 1, wherein said system includes an optical fiber for providing the first illumination field and the second illumination field to the optical assembly.

14. The system as claimed in claim 1, wherein said optical detector system substantially surrounds the focusing optics.

15. The system as claimed in claim 1, wherein said optical detector system substantially is positioned between the focusing optics and the sample, and surrounds a focal path of the focusing optics.

16. The system as claimed in claim 1, wherein said focusing optics includes a gradient index (GRIN) lens.

17. The system as claimed in claim 1, wherein said optical assembly includes a filter for passing to the optical detector only illumination from within the sample having the first optical frequency.

18. The system as claimed in claim 1, wherein said optical assembly includes a cover that is transparent to the first optical frequency and the second optical frequency to provide a sealed optical assembly.

19. The system as claimed in claim 1, wherein said optical assembly includes a light baffle for preventing illumination from contacting the optical detector that has not passed through an optical filter.

20. The system as claimed in claim 1, wherein said optical assembly includes a scanning assembly for scanning the focal area within a sample in at least one direction.

21. The system as claimed in claim 20, wherein said scanning assembly includes an electro-optical switch.

22. The system as claimed in claim 20, wherein said scanning assembly includes at least two positionable mirrors for positioning the focal area within a range of x and y directions within the sample.

23. The system as claimed in claim 20, wherein said scanning assembly includes a micro-electro-mechanical element.

24. The system as claimed in claim 23, wherein said micro-electro-mechanical element provides that the focal area may be positioned within a range of x and y directions within the sample.

25. The system as claimed in claim 20, wherein said scanning assembly includes a piezo tube actuator for positioning a tip of an optical fiber that delivers the first illumination field and the modulated second illumination field to the focal area within a range of x and y directions within the sample.

26. A method of performing microscopy or micro-spectroscopy, said method comprising the steps of:
providing a first illumination field at a first optical frequency $\omega_1$;
providing a second illumination field at a second optical frequency $\omega_2$;
modulating a property of the second illumination field at a modulation frequency f of at least 100 kHz to provide a modulated second illumination field;
directing and focusing the first illumination field and the modulated second illumination field through an objective lens toward the common focal volume along an excitation path;
detecting a detected first field intensity of the first illumination field that is back-scattered within a sample at an optical detector system that includes at least one optical detector, wherein said optical detector is positioned proximate a portion of the excitation path;
providing an electrical signal representative of the detected first field intensity; and
processing the electrical signal to detect a modulation at the frequency if of the electrical signal due to non-linear optical interaction within the common focal volume.

27. The method as claimed in claim 26, wherein said optical detector system substantially surrounds a portion of the excitation path.

28. The method as claimed in claim 26 wherein said method further includes the step of providing an output signal that is representative of one of a gain or loss of illumination at the first optical frequency $\omega_1$ due to the non-linear optical interaction within the common focal volume.

29. The method as claimed in claim 26, wherein illumination at a difference frequency between $\omega_1$ and $\omega_2$ is resonant with a molecular vibrational frequency of the sample in the focal volume.

30. The method as claimed in claim 26, wherein one of said first and second illumination fields is a broadband illumination field.

31. The method as claimed in claim 26, wherein one of the first illumination field or the second illumination field is resonant with an electronic absorption of the sample.

32. The method as claimed in claim 31, wherein the second illumination field excites molecules in the sample into an excited state.

33. The method as claimed in claim 31, wherein the second illumination field removes molecules from a ground state by promoting them to an excited state.

34. The method as claimed in claim 26, wherein a sum frequency of the first illumination field and the second illumination field is resonant with a two-photon electronic absorption of the sample.

35. The method as claimed in claim 26, wherein said method further includes the step of providing a pixel signal that is representative of the modulation at the frequency f of the electrical signal due to non-linear optical interaction within the common focal volume as a pixel for an image for an imaging system.

36. The method as claimed in claim 26, wherein said method further includes the step of filtering illumination from within the sample to pass to the optical detector only illumination having the first optical frequency.

37. The method as claimed in claim 26, wherein said method further includes the step of scanning the focal area within a sample in at least one direction.

38. The method as claimed in claim 37, wherein said step of scanning includes the step of actuating an electro-optical switch.

39. The method as claimed in claim 37, wherein said step of scanning includes the step of actuating at least two positionable mirrors for positioning the focal area within a range of x and y directions within the sample.

40. The method as claimed in claim 37, wherein said step of scanning includes the step of actuating a micro-electro-mechanical element.

41. The method as claimed in claim 40, wherein said micro-electro-mechanical element provides that the focal area may be positioned within a range of x and y directions within the sample.

42. The method as claimed in claim 26, wherein said step of scanning includes the step of actuating a piezo tube actuator for positioning a tip of an optical fiber that delivers the first illumination field and the modulated second illumination field to the focal area within a range of x and y directions within the sample.

* * * * *